(12) United States Patent
Schwender et al.

(10) Patent No.: US 6,323,206 B1
(45) Date of Patent: Nov. 27, 2001

(54) CHEMOKINE RECEPTOR ANTAGONISTS AND METHODS OF USE THEREFOR

(75) Inventors: Charles F. Schwender, Glen Gardner, NJ (US); Charles R. Mackay, Watertown, MA (US); Julia C. Pinto, Beverly Farms, MA (US); Walter Newman, Boston, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/010,321

(22) Filed: Jan. 21, 1998

Related U.S. Application Data

(63) Continuation-in-part of application No. 08/891,518, filed on Jul. 11, 1997.
(60) Provisional application No. 60/021,716, filed on Jul. 12, 1996.

(51) Int. Cl.[7] .................. A61K 31/4433; C07D 401/06
(52) U.S. Cl. ................ 514/253.03; 514/254.11; 514/291; 514/320; 514/321; 514/324; 514/325; 544/362; 544/375; 544/378; 544/380; 546/89; 546/196; 546/197; 546/202; 546/203
(58) Field of Search .................... 544/375, 380, 544/362, 378; 546/196, 202, 203, 89, 197; 514/254.11, 320, 324, 325, 253.03, 291.21

(56) References Cited

U.S. PATENT DOCUMENTS

| | | | |
|---|---|---|---|
| 3,770,729 | 11/1973 | Nakanishi et al. | 260/240 |
| 3,907,812 | 9/1975 | Yamamoto et al. | 260/293.77 |
| 3,922,266 | 11/1975 | Katsube et al. | 260/240 |

(List continued on next page.)

FOREIGN PATENT DOCUMENTS

| | | |
|---|---|---|
| 240 698 | 6/1987 | (CS) . |
| 80449 | 9/1969 | (DE) . |
| 1918739 | 10/1969 | (DE) . |
| 0 270 692 A1 | 6/1988 | (EP) . |
| 0 341 860 A1 | 11/1989 | (EP) . |
| 0 515 158 A1 | 11/1992 | (EP) . |
| 0 524 784 A1 | 1/1993 | (EP) . |
| 0916668 A1 | 5/1999 | (EP) . |
| 1213172 | 11/1970 | (GB) . |
| 1 330 966 | 12/1976 | (GB) . |
| 1109847 | 4/1996 | (GB) . |
| 62029558 | 2/1987 | (JP) . |
| 9-40662 | 2/1997 | (JP) . |
| WO 98/43638 | 10/1988 | (WO) . |
| WO 89/10369 | 11/1989 | (WO) . |
| 90/13539 | 11/1990 | (WO) . |
| WO 92/20681 | 11/1992 | (WO) . |
| WO 93/02081 | 2/1993 | (WO) . |
| 96/31470 | 10/1996 | (WO) . |
| 96/31498 | 10/1996 | (WO) . |
| WO 96/31469 | 10/1996 | (WO) . |
| WO 96/31477 | 10/1996 | (WO) . |
| WO 97/24325 | 7/1997 | (WO) . |
| WO 97/44329 | 11/1997 | (WO) . |
| WO98/02151 | 1/1998 | (WO) . |
| WO 98/04554 | 2/1998 | (WO) . |
| WO 98/27815 | 7/1998 | (WO) . |
| WO 98/46587 | 10/1998 | (WO) . |

OTHER PUBLICATIONS

Kato et al., Chemical Abstracts, vol. 130, abstract 237480, 1999.*
Kumazawa et al., Chemical Abstracts, vol. 126, abstract 212158, 1997.*
Ting et al., Chemical Abstracts, vol. 123, abstract 227838, 1995.*
Protiva et al., Chemical Abstracts, vol. 109, abstract 92794, 1988.*
Protiva et al., Chemical Abstracts, vol. 107, abstract 134327, 1987.*
Protiva et al., Chemical Abstracts, vol. 104, abstract 19527, 1986.*
Sindelar et al., Chemical Abstracts, vol. 104, abstract 33990, 1986.*
Kukla, Chemical Abstracts, vol. 92, abstract 198282, 1980.*
Protiva et al., Chemical Abstracts, vol. 72, abstract 3387, 1970.*

(List continued on next page.)

*Primary Examiner*—Richard L. Raymond
(74) *Attorney, Agent, or Firm*—Hamilton, Brook, Smith & Reynolds, P.C.

(57) ABSTRACT

Disclosed is a method of treating a subject with a disease associated with aberrant leukocyte recruitment and/or activation. The method comprises administering to the subject a therapeutically effective amount of a compound represented by the following structural formula:

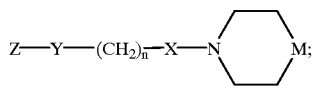

and physiologically acceptable salts thereof.

Z is a cycloalkyl or non-aromatic heterocyclic ring group fused to one or more carbocyclic aromatic rings and/or heteroaromatic rings, wherein each ring in Z is independently substituted or unsubstituted;

Y is a covalent bond, —O— or —CO—;

n is an integer from one to about five;

X is a covalent bond or —CO—; and

M is $>NR_2$, $>CR_1R_2$;

$R_1$ is —H, —OH, an aliphatic group, —O—(aliphatic group), —SH or —S—(aliphatic group);

$R_2$ is an aliphatic group, a substituted aliphatic group, an aromatic group, a substituted aromatic group, a benzylic group, a substituted benzylic group, a non-aromatic heterocyclic group or a substituted non-aromatic heterocyclic group.

19 Claims, 9 Drawing Sheets

U.S. PATENT DOCUMENTS

| | | | |
|---|---|---|---|
| 3,936,468 | 2/1976 | Yamamoto et al. | 260/293.84 |
| 4,086,234 | 4/1978 | Dryden et al. | 260/268 |
| 4,125,612 | 11/1978 | Sherlock | 424/250 |
| 4,250,176 | 2/1981 | Vandenberk et al. | 424/250 |
| 4,335,122 | 6/1982 | McFadden et al. | 424/244 |
| 4,547,496 | 10/1985 | Kumazawa et al. | 514/218 |
| 4,645,758 | 2/1987 | Willman et al. | 514/239 |
| 4,994,463 | 2/1991 | Oshima et al. | 514/253 |
| 4,999,363 | 3/1991 | Oshima et al. | 514/332 |
| 5,010,087 | 4/1991 | Oshima et al. | 514/307 |
| 5,010,104 | 4/1991 | Oshima et al. | 514/510 |
| 5,089,496 | 2/1992 | Piwinski et al. | 514/253 |
| 5,116,863 | 5/1992 | Oshima et al. | 514/450 |
| 5,118,701 | 6/1992 | Oshima et al. | 514/395 |
| 5,143,922 | 9/1992 | Oshima et al. | 514/320 |
| 5,242,931 | 9/1993 | Oshima et al. | 514/307 |
| 5,302,596 | 4/1994 | Oshima et al. | 514/261 |
| 5,302,602 | 4/1994 | Oshima et al. | 514/325 |
| 5,340,807 | 8/1994 | Kumazawa et al. | 514/215 |
| 5,378,701 | 1/1995 | Ohshima et al. | 514/215 |
| 5,478,835 | 12/1995 | Kumazawa et al. | 514/290 |
| 5,478,840 | 12/1995 | Ohshima et al. | 514/303 |
| 5,538,986 * | 7/1996 | Ting et al. | 514/337 |
| 5,607,955 | 3/1997 | Ohshima et al. | 514/359 |
| 5,672,611 | 9/1997 | Doll et al. | 514/325 |
| 5,679,703 | 10/1997 | Yanase et al. | 514/431 |
| 5,688,788 | 11/1997 | Anderson et al. | 514/211 |
| 5,801,175 | 9/1998 | Afonso et al. | 514/254 |
| 5,874,428 | 2/1999 | Dørwald et al. | 514/217 |
| 5,877,177 | 3/1999 | Taveras | 514/254 |
| 6,040,318 | 3/2000 | Andersen et al. | 514/329 |
| 6,048,856 | 4/2000 | Jørgensen et al. | 514/217 |
| 6,150,355 | 11/2000 | Kumazawa et al. | 514/215 |

OTHER PUBLICATIONS

Davis et al., Chemical Abstracts, vol. 67, abstract 99959, 1967.*

Davis, M.A., "Analogs of Amitriptyline Containing the Normeperidine Group," *J. Med. Chem.*, 10:627–635 (Jul. 1967).

Šindelář, K., et al., "Potential Antidiarrheal Agents: 1-(11-Cyano-6,11-Dihydrodibenzo[b,e] Thiepin-10-Yl-Alkyl) and 1-(10-Cyano-10,11-Dihydrodibenzo[b,f] Thiepin-10-Yl-Alkyl)-4-Substituted Piperdines," *Czechoslovak Chem. Commun.*, 50:1089–1096 (1985).

Helwig, H., et al., "Helwig/Otto Arzneimittel", *Arzneimittel, 1*:4–1 through 4–24, 8th Ed., (1992).

Nakagawa, A., et al., "Synthesis of 2,3,17β-Trihydroxyestra-1,3,5(10)-trien-6-one and its Related Compounds," *Chem. Pharm. Bull.,* 26(1):3567–3571 (1978).

* cited by examiner

Example 1

Example 2

Example 3

Example 4

Example 5

Example 6

Example 7

Example 8

Example 9

Example 10

Example 11

Example 12

Example 13

Example 14

Example 15

Example 16

Example 17

Example 18

Example 19

Example 20

Example 21

Example 22

Example 23

Example 24

Example 25　　　　　Example 26　　　　　Example 27

Example 28　　　　　Example 29　　　　　Example 30

Example 31　　　　　Example 32　　　　　Example 33

Example 34　　　　　Example 35　　　　　Example 36

Example 37

Example 38

Example 39

Example 40

Example 41

Example 42

Example 43

Example 44

Example 45

Example 46

Example 47

Example 48

Example 49

Example 50

Example 51

Example 52

Example 53

Example 54

Example 55

Example 56

Example 57

Example 58

Example 59

CHEMOKINE RECEPTOR ANTAGONISTS AND METHODS OF USE THEREFOR

RELATED APPLICATIONS

This application is a continuation-in-part of U.S. Ser. No. 08/891,518, filed Jul. 11, 1997, which claims priority to U.S. provisional application Ser. No. 60/021,716, filed Jul. 12, 1996, the entire teachings of which are hereby incorporated by reference.

BACKGROUND OF THE INVENTION

Chemoattractant cytokines or chemokines are a family of proinflammatory mediators that promote recruitment and activation of multiple lineages of leukocytes and lymphocytes. They can be released by many kinds of tissue cells after activation. Continuous release of chemokines at sites of inflammation mediates the ongoing migration of effector cells in chronic inflammation. The chemokines characterized to date are related in primary structure. They share four conserved cysteines, which form disulfide bonds. Based upon this conserved cysteine motif, the family is divided into two main branches, designated as the C—X—C chemokines ($\alpha$-chemokines), and the C—C chemokines ($\beta$-chemokines), in which the first two conserved cysteines are separated by an intervening residue, or adjacent respectively (Baggiolini, M. and Dahinden, C. A., *Immunology Today*, 15:127–133 (1994)).

The C—X—C chemokines include a number of potent chemoattractants and activators of neutrophils, such as interleukin 8 (IL-8), PF4 and neutrophil-activating peptide-2 (NAP-2). The C—C chemokines include RANTES (Regulated on Activation, Normal T Expressed and Secreted), the macrophage inflammatory proteins 1$\alpha$ and 1$\beta$ (MIP-1$\alpha$ and MIP-1$\beta$), and human monocyte chemotatic proteins 1–3 (MCP-1, MCP-2, MCP-3), which have been characterized as chemoattractants and activators of monocytes or lymphocytes but do not appear to be chemoattractants for neutrophils. Chemokines, such as RANTES and MIP-1$\alpha$, have been implicated in a wide range of human acute and chronic inflammatory diseases including respiratory diseases, such as asthma and allergic disorders.

The chemokine receptors are members of a superfamily of G protein-coupled receptors (GPCR) which share structural features that reflect a common mechanism of action of signal transduction (Gerard, C. and Gerard, N. P., *Annu Rev. Immunol.*, 12:775–808 (1994); Gerard, C. and Gerard, N. P., *Curr. Opin. Immunol.*, 6:140–145 (1994)). Conserved features include seven hydrophobic domains spanning the plasma membrane, which are connected by hydrophilic extracellular and intracellular loops. The majority of the primary sequence homology occurs in the hydrophobic transmembrane regions with the hydrophilic regions being more diverse. The first receptor for the C—C chemokines that was cloned and expressed binds the chemokines MIP-1$\alpha$ and RANTES. Accordingly, this MIP-1$\alpha$/RANTES receptor was designated C—C chemokine receptor 1 (also referred to as CCR-1; Neote, K., et al., *Cell*, 72:415–425 (1993); Horuk, R. et al., WO 94/11504, May 26, 1994; Gao, J.-I. et al., *J. Exp. Med.*, 177:1421–1427 (1993)). Three new receptors have been characterized which bind and/or signal in response to RANTES: CCR3 mediates binding and signaling of chemokines including eotaxin, RANTES, and MCP-3 (Ponath et al., *J. Exp. Med.*, 183:2437 (1996)), CCR4 binds chemokines including RANTES, MIP-1$\alpha$, and MCP-1 (Power, et al., *J. Biol. Chem.*, 270:19495 (1995)), and CCR5 binds chemokines including MIP-1$\alpha$, RANTES, and MIP-1$\beta$ (Samson, et al., *Biochem.* 35: 3362–3367 (1996)). RANTES is a chemotactic chemokine for a variety of cell types, including monocytes, eosinophils, and a subset of T-cells. The responses of these different cells may not all be mediated by the same receptor, and it is possible that the receptors CCR1, CCR4 and CCR5 will show some selectivity in receptor distribution and function between leukocyte types, as has already been shown for CCR3 (Ponath et al.). In particular, the ability of RANTES to induce the directed migration of monocytes and a memory population of circulating T-cells (Schall, T. et al., *Nature*, 347:669–71 (1990)) suggests this chemokine and its receptor(s) may play a critical role in chronic inflammatory diseases, since these diseases are characterized by destructive infiltrates of T cells and monocytes.

Many existing drugs have been developed as antagonists of the receptors for biogenic amines, for example, as antagonists of the dopamine and histamine receptors. No successful antagonists have yet been developed to the receptors for the larger proteins such as chemokines and C5a. Small molecule antagonists of the interaction between C—C chemokine receptors and their ligands, including RANTES and MIP-1$\alpha$, would provide compounds useful for inhibiting harmful inflammatory processes "triggered" by receptor ligand interaction, as well as valuable tools for the investigation of receptor-ligand interactions.

SUMMARY OF THE INVENTION

It has now been found that a number of small organic molecules are antagonists of chemokine receptor function and can inhibit leukocyte activation and/or recruitment. An antagonist of chemokine receptor function is a molecule which can inhibit the binding of one or more chemokines, including C—C chemokines such as RANTES and/or MIP-1$\alpha$, to one or more chemokine receptors on leukocytes and/or other cell types. As a consequence, processes and cellular responses mediated by chemokine receptors can be inhibited with these small organic molecules. Based on this discovery, a method of treating a subject with a disease associated with aberrant leukocyte recruitment and/or activation is disclosed. The method comprises administering to the subject a therapeutically effective amount of a compound or small organic molecule which is an antagonist of chemokine receptor function. Compounds or small organic molecules which have been identified as antagonists of chemokine receptor function are discussed in detail hereinbelow, and can be used for the manufacture of a medicament for treating or for preventing a disease associated with aberrant leukocyte recruitment and/or activation. The invention also relates to the disclosed compounds and small organic molecules for use in treating or preventing a disease associated with aberrant leukocyte recruitment and/or activation. The invention also includes pharmaceutical compositions comprising one or more of the compounds or small organic molecules which have been identified herein as antagonists of chemokine function and a suitable pharmaceutical carrier. The invention further relates to novel compounds which can be used to treat an individual with a disease associated with aberrant leukocyte recruitment and/or activation.

DETAILED DESCRIPTION OF THE INVENTION

Figure 1:
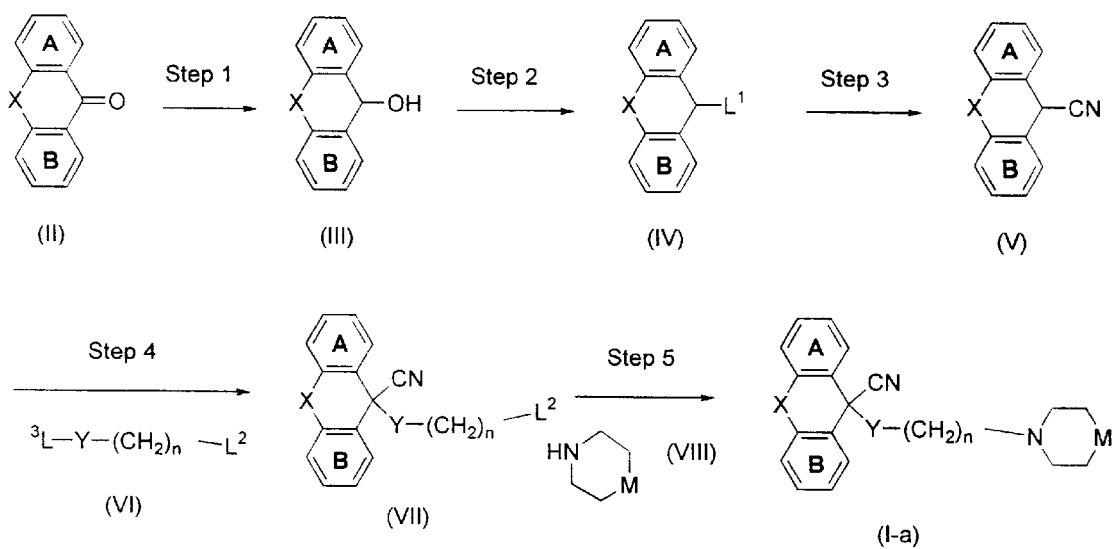
FIG. 1 is a schematic showing the preparation of the compounds represented by Structural Formulas (I) and (II).

The present invention relates to small molecule compounds which are antagonists of chemokine receptor function. Accordingly, processes or cellular responses mediated by the binding of a chemokine to a receptor can be inhibited (reduced or prevented, in whole or in part), including leukocyte migration, integrin activation, transient increases in the concentration of intracellular free calcium [Ca$^{++}$]$_i$, and/or granule release of proinflammatory mediators.

The invention further relates to a method of treatment, including prophylactic and therapeutic treatments, of a disease associated with aberrant leukocyte recruitment and/or activation, including chronic inflammatory disorders characterized by the presence of RANTES and/or MIP-1α responsive T cells, monocytes and/or eosinophils, including but not limited to diseases such as arthritis, psoriasis, multiple sclerosis, inflammatory bowel diseases such as ulcerative colitis and Crohn's disease, as well as allergies and asthma. Other diseases associated with aberrant leukocyte recruitment and/or activation which can be treated (including prophylactic treatments) with the methods disclosed herein are inflammatory diseases associated with Human Immunodeficiency Virus (HIV) infection, e.g., AIDS associated encephalitis, AIDS related maculopapular skin eruption, AIDS related interstitial pneumonia, AIDS related enteropathy, AIDS related periportal hepatic inflammation and AIDS related glomerulo nephritis. The method comprises administering to a subject a therapeutically effective amount of a compound (i.e., one or more compounds) which inhibits chemokine receptor function, inhibits the binding of a chemokine to leukocytes and/or other cell types, and/or which inhibits leukocyte migration to, and/or activation at, sites of inflammation. According to the method, chemokine-mediated chemotaxis and/or activation of pro-inflammatory cells bearing receptors for chemokines can be inhibited. As used herein, "pro-inflammatory cells" includes but is not limited to leukocytes, since chemokine receptors may be expressed on other cell types, such as neurons and epithelial cells.

In one embodiment of the present invention, the antagonist of chemokine receptor function is represented by Structural Formula (I):

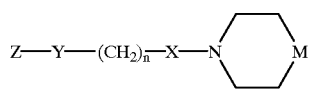

(I)

Z is a cycloalkyl or non-aromatic heterocyclic ring fused to one or more carbocyclic aromatic rings and/or heteroaromatic rings.

Y is a covalent bond, —O— or —CO—.

n is an integer from one to about five. n is preferably one, two, or three.

X is a covalent bond or —CO—.

M is >NR$_2$ or >CR$_1$R$_2$. Preferably, M is >C(OH)R$_2$.

R$_1$ is —H, —OH, an aliphatic group, —O—(aliphatic group), —SH or —S—(aliphatic group). Preferably, R$_1$ is —H or —OH.

R$_2$ is an aliphatic group, a substituted aliphatic group, an aromatic group, a substituted aromatic group, a benzylic group, a substituted benzylic group, a non-aromatic heterocyclic group or a substituted non-aromatic heterocyclic group. Preferably, R$_2$ is an aromatic or a substituted aromatic group.

In a preferred embodiment, —X— and —Y— in Structural Formula (I) are each a covalent bond and the antagonist of chemokine receptor function is a compound represented by Structural Formula (II):

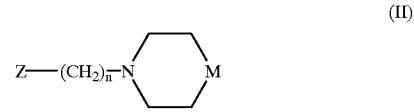

(II)

Z, n and M are as described above for Structural Formula (I).

In another preferred embodiment, —X— is a covalent bond, —Y— is —CO— and the antagonist of chemokine receptor function is a compound represented by Structural Formula (III):

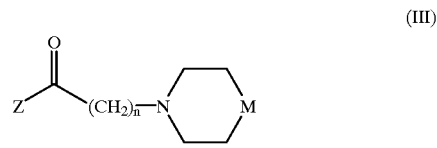

(III)

Preferably, Z is a tricyclic ring system comprising two carbocyclic aromatic groups fused to a seven or eight membered cycloalkyl group or to a non-aromatic heterocyclic ring. In one example, Z is represented by Structural Formula (IV):

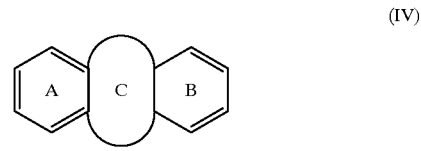

(IV)

The phenyl rings in Structural Formula (IV), labeled with an "A" and "B", are referred to herein as "Ring A" and "Ring B", respectively. The central ring, labeled with a "C", is referred to as "Ring C" and can be, for example a seven or eight membered non-aromatic carbocyclic ring (e.g., a cycloheptane or cyclooctane ring) or a non-aromatic heterocyclic ring. When Ring C is a non-aromatic heterocyclic ring, it can contain one or two heteroatoms such as nitrogen, sulfur or oxygen. When Z is represented by Structural Formula (IV), the tricyclic ring system is connected to Y in Structural Formula (I) by a single covalent bond between Y and a ring atom in Ring C.

Ring A and/or Ring B can be unsubstituted. Alternatively, Ring A and/or Ring B can have one or more substituents. Suitable substituents are as described hereinbelow for substituted aromatic groups. In one example, Ring A or Ring B is substituted with —$(CH_2)_t$—COOH, —$(CH_2)_t$—COOR$^{20}$ or —$(CH_2)_t$—C(O)—NR$^{21}$R$^{22}$.

t is an integer from zero to about 3.

$R^{20}$, $R^{21}$ or $R^{22}$ are independently —H, an aliphatic group a substituted aliphatic group, an aromatic group, a substituted aromatic group, —NHC(O)—O—(aliphatic group), —NHC(O)—O—(aromatic group) or —NHC(O)—O—(non-aromatic heterocyclic group). In addition, $R^{21}$ and $R^{22}$, taken together with the nitrogen atom to which they are bonded, can form a non-aromatic heterocyclic ring.

Ring C optionally contains one or more additional substituents. When Ring C is a non-aromatic carbocyclic ring, suitable substituents are as described hereinbelow for substituted aliphatic groups. When Ring C contains one or more heteroatoms, suitable substituents are as described below for non-aromatic heterocyclic rings. Preferably, Ring C is unsubstituted or substituted with an electron withdrawing group. Suitable electron withdrawing groups include —CN, alkylsulfonyl, carboxamido, carboxylic alkyl esters, —$NO_2$ and halogens (e.g., —Br and —Cl). Alternatively, Ring C is substituted with a group selected from —$CH_2$—$NR^{11}R^{12}$, —$CH_2$—$OR^{11}$, —$CH_2$—NH—CO—$NR^{11}R^{12}$, —$CH_2$—O—CO—$NR^{11}R^{12}$.

$R^{11}$ and $R^{12}$ are independently —H, an aliphatic group a substituted aliphatic group, an aromatic group, a substituted aromatic group, —NHC(O)—O—(aliphatic group), or NHC(O)—O—(aromatic group). In addition, $R^{11}$ and $R^{12}$, taken together with the nitrogen atom to which they are bonded, can form a non-aromatic heterocyclic ring.

Examples of suitable tricyclic rings systems represented by Structural Formula (IV) are provided by Structural Formula (V)–(VIII), shown below:

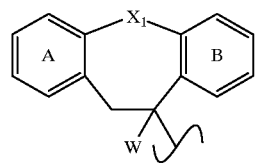
(V)

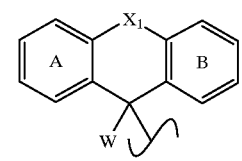
(VI)

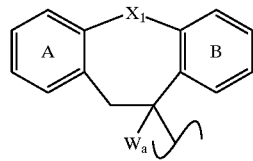
(VII)

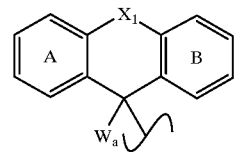
(VIII)

$X_1$ is a chemical bond, —S—, —$CH_2$— or —$CH_2S$—. Preferably, $X_1$ is —S— in Structural Formulas (V) and (VII). Preferably, $X_1$ is —$CH_2S$— in Structural Formulas (VI) and (VIII).

W is —H or an electron withdrawing group, as described above for Structural Formula (IV). A preferred electron withdrawing group is —CN.

$W_a$ is a group selected from —$CH_2$—$NR^{11}R_{12}$, —$CH_2$—$OR^{11}$, —$CH_2$—NH—CO—$NR^{11}R^{12}$ or —$CH_2$—O—CO—$NR^{11}R^{12}$. $R^{11}$ and $R^{12}$ are as defined in Structural Formula (IV).

Ring A and Ring B in Structural Formulas (V)–(VIII) are as described above in Structural Formula (IV).

Other examples of suitable tricyclic ring systems represented by Structural Formula (IV) are shown below in Structural Formulas (IX)–(XII), (XIIa), (XIIb) an (XIIc):

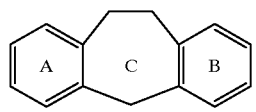
(IX)

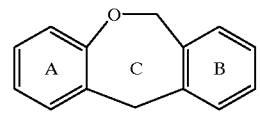
(X)

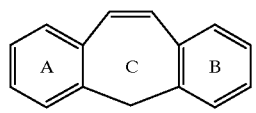
(XI)

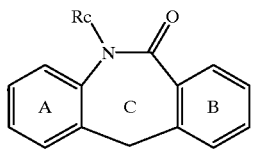
(XII)

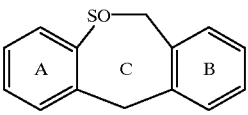
(XIIa)

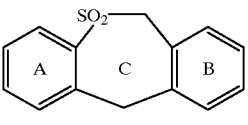
(XIIb)

(XIIc)

Rings A–C in Structural Formulas (IX)-(XII), (XIIa), (XIIb) and (XIIc) are as described for Structural Formula (IV).

$R_c$ is an aliphatic group, a substituted aliphatic group, an aromatic group, a substituted aromatic group, a benzylic group or a substituted benzylic group. Preferably, $R_c$ is a substituted C1–C20 aliphatic group, a C10–C20 aliphatic group, an aromatic group, a substituted aromatic group, a benzylic group or a substituted benzylic group. In one example, $R_c$ is —$(CH_2)_s$—COOH, —$(CH_2)_s$—$COOR^{30}$ or —$(CH_2)_s$—C(O)—$NR^{31}R^{32}$.

s is an integer from zero to about 3.

$R^{30}$, $R^{31}$ and $R^{32}$ are independently —H, an aliphatic group a substituted aliphatic group, an aromatic group, a substituted aromatic group, —NHC(O)—O—(aliphatic group), —NHC(O)—O—(aromatic group) or —NHC(O)—O—(non-aromatic heterocyclic group). In addition, $R^{31}$ and $R^{32}$, taken together with the nitrogen atom to which they are bonded, can form a non-aromatic heterocyclic ring.

Preferred examples of tricyclic ring systems represented by Structural Formulas (IX)–(XII),(XIIa), (XIIb) and (XIIc) are shown below in Structural Formulas (XIII)–(XVI), (XVIa), (XVIb) and (XVIc):

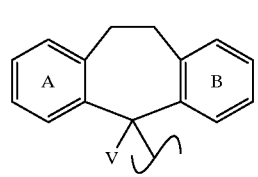
(XIII)

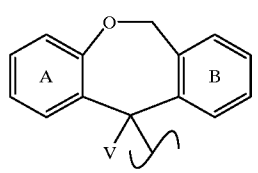
(XIV)

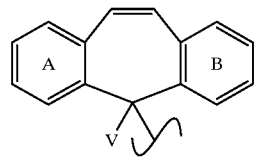
(XV)

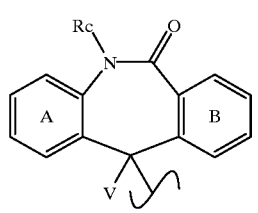
(XVI)

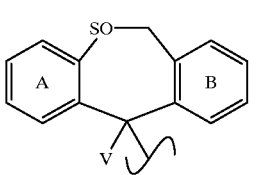
(XVIa)

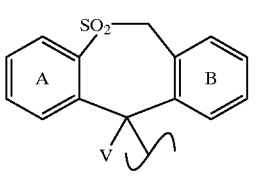
(XVIb)

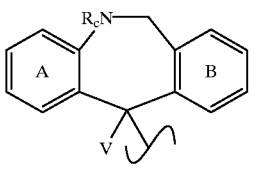
(XVIc)

V is W or $W_a$, which are as described above for Structural Formula (V)–(VIII).

In another preferred embodiment, Z is a tricyclic ring system comprising one or more heteroaromatic groups fused to a seven or eight membered cycloalkyl group or to a non-aromatic heterocyclic ring. Examples are represented by Structural Formulas (XVII)–(XXI), (XXIa), (XXIb) and (XXIc):

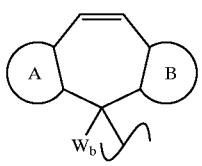
(XVII)

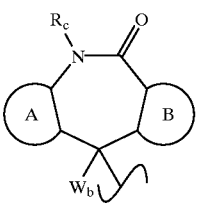
(XVIII)

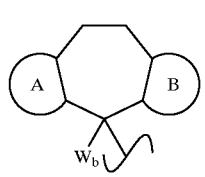
(XIX)

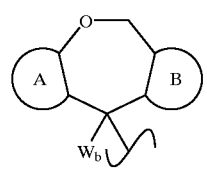
(XX)

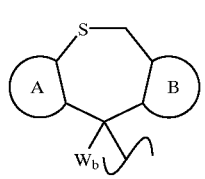
(XXI)

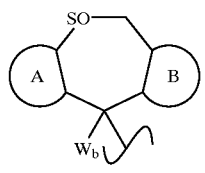
(XXIa)

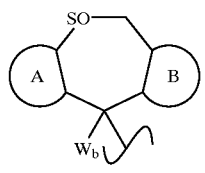
(XXIb)

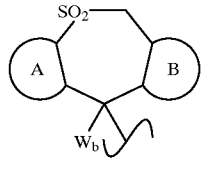
(XXIc)

Ring A in Structural Formulas (XVII)–(XXI), (XXIa), (XXIb) and (XXIc) is a substituted or unsubstituted aromatic group.

Ring B in Structural Formulas (XVII)–(XXI), (XXIa), (XXIb) and (XXIc) is a substituted or unsubstituted heteroaryl group.

$W_b$ is —H, —CN, —CH$_2$—NR$^{11}$R$^{12}$, —CH$_2$—OR$^{11}$, —CH$_2$—NH—CO—NR$^{11}$R$^{12}$, —CH$_2$—O—CO—NR$^{11}$R$^{12}$. R$^{11}$ and R$^{12}$ are as defined above for Structural Formula (IV).

In yet another preferred embodiment, the antagonist of chemokine function is a compound represented by Structural Formula (XXII and (XXIII):

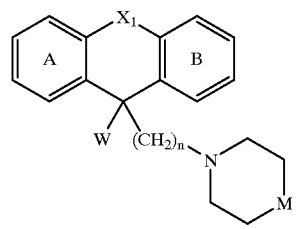

(XXII)

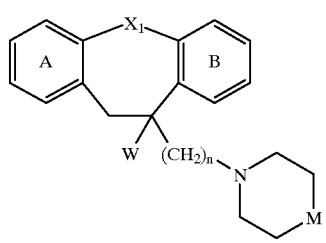

(XXIII)

In Structural Formulas (XXII) and (XXIII), $X_1$ is as defined above for Structural Formulas (V) and (VI); n is an integer from two to five; W is —H, —CN, alkylsulfonyl, carboxamido or carboxyalkyl.

In Structural Formulas (XXII) and (XXIII), Ring A is substituted with $R_8$ and $R_9$, wherein $R_8$ and $R_9$ are independently —H, a halogen, alkoxy or alkyl, or, taken together with ring A, form a naphthyl group. M is >N(alkanoyl), >N(aroyl), >N(aralkoyl), >N(alkyl), >N(aralkyl), >N(cycloalkyl), >C(OH)(aryl) or >CH(heteroaryl).

The present invention also includes novel compounds represented by Structural Formulas (II) and (III).

In one embodiment, the novel compounds are represented by Structural Formulas (II) and (III) wherein Z is a group in which one or more heteroaromatic rings are fused to a cycloalkyl ring or a non-aromatic heterocyclic ring. Each ring in Z is independently substituted or unsubstituted. Examples of suitable Z groups are represented by Structural Formulas (XVII)–(XXI), (XXIa), (XXIb) and (XXIc). Ring A, Ring B, M, $W_b$, $R_1$, $R_2$, $R_c$ and n are as described in Structural Formulas (XVII) through (XXIc).

In another embodiment, the novel compounds are represented by Structural Formulas (II) and (III) have a Z group represented by Structural Formulas (V) and (VI). At least one of Ring A or Ring B is substituted. M, W, $R_1$, $R_2$ and n are as described in Structural Formulas (V) and (VI).

In another embodiment, the novel compounds represented by Structural Formulas (II) and (III) have a Z group represented by Structural Formulas (VII) and (VIII). Ring A, Ring B, M, $W_a$, $R_1$, $R_2$ and n are as described in Structural Formulas (VII) and (VIII).

In another embodiment, the novel compounds represented by Structural Formulas (II) and (III) have a Z group represented by Structural Formulas (XIII)–(XVI), (XVIa), (XVIb) and (XVIc). Ring A, Ring B, M, $R_1$, $R_2$, $R_c$ and n are as described in Structural Formulas (XIII) through (XVIc). V is —CN, —CH$_2$—NR$^{11}$R$^{12}$, —CH$_2$—OR$^{11}$, —CH$_2$—NH—CO—NR$_{11}$R$^{12}$, —CH$_2$—O—CO—NR$^{11}$R$^{12}$. R$^{11}$ and R$^{12}$ are defined above for Structural Formula (IV).

In another embodiment, the novel compounds represented by Structural Formulas (II) and (III) have a Z group represented by Structural Formula (XVI). Ring A, Ring B, M, $R_1$, $R_2$, and n are as described in Structural Formula (XVI). V is —H and $R_c$ is a C10–C20 aliphatic group, a substituted C10–C20 aliphatic group, an aromatic group, a substituted aromatic group, a benzylic group or a substituted benzylic group. In one example, $R_c$ is —(CH$_2$)$_s$—COOH, —(CH$_2$)$_s$—COOR$^{30}$ or —(CH$_2$)$_s$—C(O)—NR$^{31}$R$^{32}$, wherein s, R$^{30}$, R$^{31}$ and R$^{32}$ are as desribed above. Preferably, $R_c$ is an aromatic group, a substituted aromatic group, a benzylic group or a substituted benzylic group.

In yet another embodiment, the novel compounds represented by Structural Formula (II) and (III) have a Z group represented by Structural Formulas (XXII) and (XXIII). Ring A, Ring B, M, W, and n are as described in Structural Formulas (XXII) through (XXIII) . $R_8$ and $R_9$ are independently a halogen, alkoxy or alkyl, or, taken together with ring A, form a naphthyl group.

Also included in the present invention are physiologically acceptable salts of the compounds represented by Structural Formulas (I) through (XXIII). Salts of compounds containing an amine or other basic group can be obtained, for example, by reacting with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like. Salts of compounds containing a carboxylic acid or other acidic functional group can be prepared by reacting with a suitable base, for example, a hydroxide base. Salts of acidic functional groups contain a countercation such as sodium, potassium and the like.

As used herein, aliphatic groups include straight chained, branched or cyclic $C_1$–$C_8$ hydrocarbons which are completely saturated or which contain one or more units of unsaturation.

An "alkyl group" is a saturated aliphatic group, as defined above. The term "alkoxy" refers to an alkyl ether chain with an alkyl group. "Alkanoyl" refers to alkyl substituted carbonyl; "aralkanoyl" refers to phenyl-alkyl—CO— and "aroyl" refers to arylcarbonyl including benzoyl, naphthoyl and the like. The term "halogen" means fluoro, chloro, bromo and iodo. The term "aryl", as opposed to the term "aromatic group", means phenyl. The term "substituted phenyl" means aryl substituted by alkyl, halogen, alkoxy, nitro, amino, acetamido, cyano and trifluoromethyl and naphthyl. "Aralkyl" means —(CH$_2$)$_x$-phenyl, wherein x is an integer from one to four including benzyl. It is noted that the terms "aromatic group", "carbocylic aromatic group" and "heterocyclic aromatic group" are defined below and have different meanings from the term "aryl".

Aromatic groups include carbocyclic aromatic groups such as phenyl, 1-naphthyl, 2-naphthyl, 1-anthracyl and 2-anthacyl, and heterocyclic aromatic groups such as N-imidazolyl, 2-imidazole, 2-thienyl, 3-thienyl, 2-furanyl, 3-furanyl, 2-pyridyl, 3-pyridyl, 4-pyridyl, 2-pyrimidy, 4-pyrimidyl, 2-pyranyl, 3-pyranyl, 3-pyrazolyl, 4-pyrazolyl, 5-pyrazolyl, 2-pyrazinyl, 2-thiazole, 4-thiazole, 5-thiazole, 2-oxazolyl, 4-oxazolyl and 5-oxazolyl.

Aromatic groups also include fused polycyclic aromatic ring systems in which a carbocyclic aromatic ring or heteroaryl ring is fused to one or more other heteroaryl rings. Examples include 2-benzothienyl, 3-benzothienyl, 2-benzofuranyl, 3-benzofuranyl, 2-indolyl, 3-indolyl, 2-quinolinyl, 3-quinolinyl, 2-benzothiazole, 2-benzooxazole, 2-benzimidazole, 2-quinolinyl, 3-quinolinyl, 1-isoquinolinyl, 3-quinolinyl, 1-isoindolyl, 3-isoindolyl, and acridintyl. Also included within the scope of the term "aromatic group", as it is used herein, is a group in which one or more carbocyclic aromatic rings and/or heteroaromatic rings are fused to a cycloalkyl or non-aromatic heterocyclic ring. Examples include decalin, phthalimido, benzodiazepines, benzooxazepines, benzooxazines, phenothiazines, and groups represented by the following structural formulas:

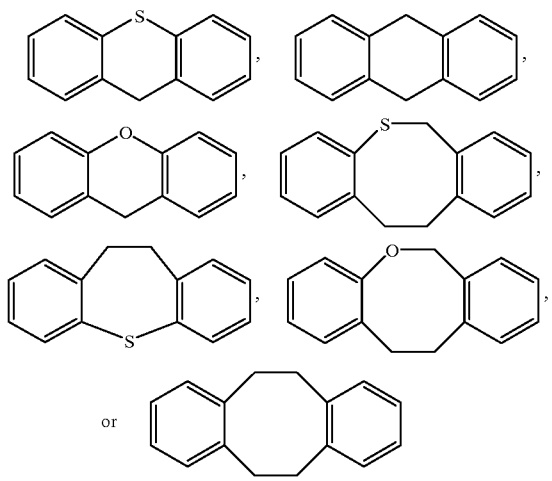

Non-aromatic heterocyclic rings are non-aromatic carbocyclic rings which include one or more heteroatoms such as nitrogen, oxygen or sulfur in the ring. The ring can be five, six, seven or eight-membered. Examples include 2-tetrahydrofuranyl, 3-tetrahydrofuranyl, 2-tetrahyrothiophenyl, 3-tetrahyrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl and 4-thiazolidinyl.

"Heterocyclic ring", as opposed to "heteroaryl group" and "non-aromatic heterocylic ring", is defined as imidazole, benzimidazole, pyridine, pyrimidine, thiazole, benzothiazole, thienyl, benzothienyl. It is noted further the terms "heterocyclic aromatic group" and "non-aromatic heterocyclic ring" are defined above and have different meanings from the term "heterocyclic ring".

Suitable substituents on an alkyl, aliphatic, aromatic, non-aromatic heterocyclic ring or benzyl group include, for example, —OH, halogen (—Br, —Cl, —I and —F) —O(aliphatic, substituted aliphatic, benzyl, substituted benzyl, aromatic or substituted aromatic group), —CN, —NO$_2$, —COOH, —NH$_2$, —NH(aliphatic group, substituted aliphatic, benzyl, substituted benzyl, aromatic or substituted aromatic group), —N(aliphatic group, substituted aliphatic, benzyl, substituted benzyl, aromatic or substituted aromatic group)$_2$, —COO(aliphatic group, substituted aliphatic, benzyl, substituted benzyl, aromatic or substituted aromatic group), —CONH$_2$, —CONH(aliphatic, substituted aliphatic group, benzyl, substituted benzyl, aromatic or substituted aromatic group)), —SH, —S(aliphatic, substituted aliphatic, benzyl, substituted benzyl, aromatic or substituted aromatic group) and —NH—C(=NH) —NH$_2$. A substituted non-aromatic heterocyclic ring, benzylic group or aromatic group can also have an aliphatic or substituted aliphatic group as a substituent. A substituted alkyl or aliphatic group can also have a non-aromatic heterocyclic ring, benzyl, substituted benzyl, aromatic or substituted aromatic group as a substituent. A substituted non-aromatic heterocyclic ring can also have =O, =S, =NH or =N(aliphatic, aromatic or substituted aromatic group) as a substituent. A substituted aliphatic, substituted aromatic, substituted non-aromatic heterocyclic ring or substituted benzyl group can have more than one substituent.

In the structural formulas depicted herein, the single or double bond by which a chemical group or moiety is connected to the remainder of the molecule or compound is indicated by the following symbol:

"$\mathcal{\zeta}$"

For example, the corresponding symbol in Structural Formula (V) or (VIII) indicates that the tricyclic ring system, which respresents Z in Structural Formula (I), is connected to the alkylene group in Structural Formula (I) by a single covalent bond between the alkylene group and the ring carbon in Ring C which is bonded to W.

A "subject" is preferably a mammal, such as a human, but can also be an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like).

A "therapeutically effective amount" of a compound is an amount which results in the inhibition of one or more processes mediated by the binding of a chemokine to a receptor in a subject with a disease associated with aberrant leukocyte recruitment and/or activation. Examples of such processes include leukocyte migration, integrin activation, transient increases in the concentration of intracellular free calcium [Ca$^{2+}$]$_i$ and granule release of proinflammatory mediators. Alternatively, a "therapeutically effective amount" of a compound is a quantity sufficient to achieve a desired therapeutic and/or prophylactic effect, such as an amount which results in the prevention of or a decrease in the symptoms associated with a disease associated with aberrant leukocyte recruitment and/or activation.

The amount of compound administered to the individual will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. Typically, a therapeutically effective amount of the compound can range from about 0.1 mg per day to about 100 mg per day for an adult. Preferably, the dosage ranges from about 1 mg per day to about 100 mg per day. An antagonist of chemokine receptor function can also be administered in combination with one or more additional therapeutic agents, e.g. theophylline, β-adrenergic bronchdilators, corticosteroids, antihistamines, antiallergic agents and the like.

The compound can be administered by any suitable route, including, for example, orally in capsules, suspensions or tablets or by parenteral administration. Parenteral administration can include, for example, systemic administration, such as by intramuscular, intravenous, subcutaneous, or intraperitoneal injection. The compound can also be administered orally (e.g., dietary), topically, by inhalation (e.g., intrabronchial, intranasal, oral inhalation or intranasal drops), or rectally, depending on the disease or condition to be treated. Oral or parenteral administration are preferred modes of administration.

The compound can be administered to the individual in conjunction with an acceptable pharmaceutical carrier as part of a pharmaceutical composition for treatment of HIV infection, inflammatory disease, or the other diseases discussed above. Formulation of a compound to be administered will vary according to the route of administration selected (e.g., solution, emulsion, capsule). Suitable pharmaceutical carriers may contain inert ingredients which do not interact with the compound. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986).

The activity of compounds of the present invention can be assessed using suitable assays, such as receptor binding assays and chemotaxis assays. For example, as described in the Exemplification Section, small molecule antagonists of RANTES and MIP-1α binding have been identified utilizing THP-1 cells which bind RANTES and chemotax in response to RANTES and MIP-1α as a model for leukocyte chemotaxis. Specifically, a high through-put receptor binding assay, which monitors $^{125}$I-RANTES and $^{125}$I-MIP-1α binding to THP-1 cell membranes, was used to identify small molecule antagonists which block binding of RANTES and MIP-1α. Compounds of the present invention can also be identified by virtue of their ability to inhibit the activation steps triggered by binding of a chemokine to its receptor, such as chemotaxis, integrin activation and granule mediator release. They can also be identified by virtue of their ability to block RANTES and MIP-1α mediated HL-60, T-cell, peripheral blood mononuclear cell, and eosinophil chemotactic response.

Figure 2:
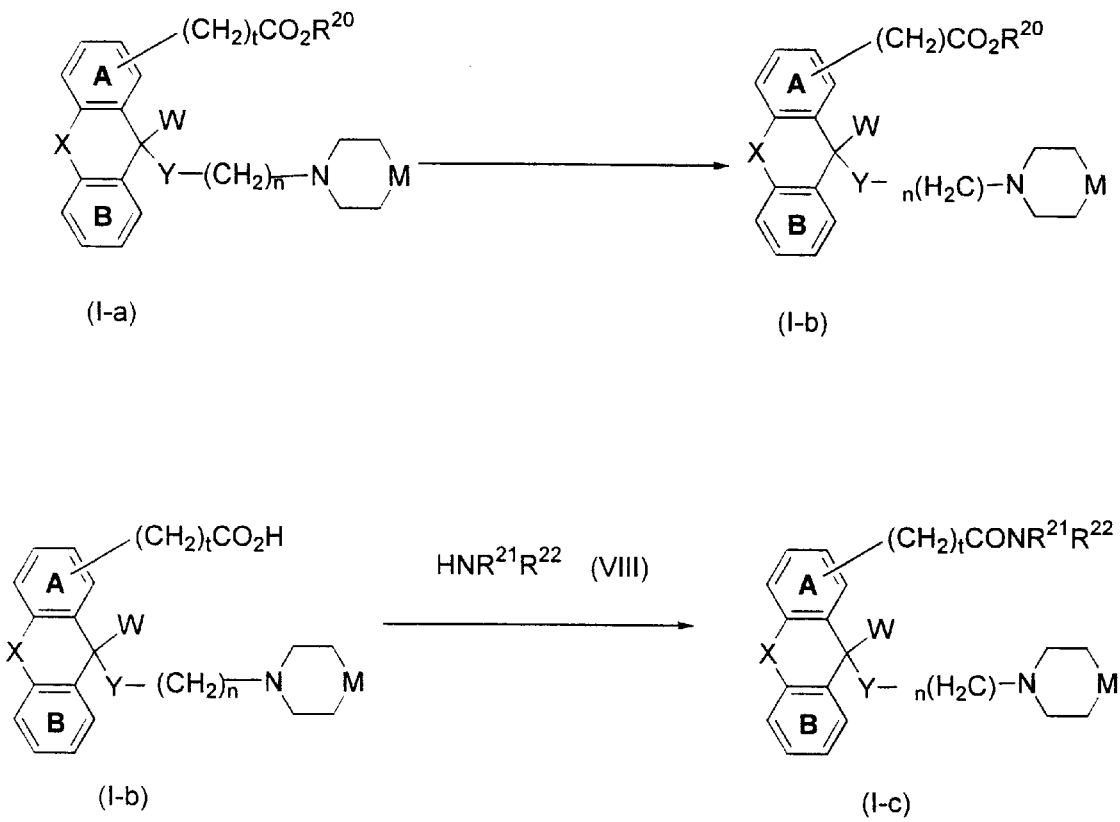
FIG. 2 is a schematic showing the preparation of the compounds represented by Structural Formula ((I) and II), wherein Z is represented by Structural Formulas (IV) and wherein Ring A in Z is substituted with —$(CH_2)_t$—COOH, —$(CH_2)_t$—COOR$^{20}$ or —$(CH_2)_t$—C(O)—NR$^{21}$R$^{22}$.
Figure 3:
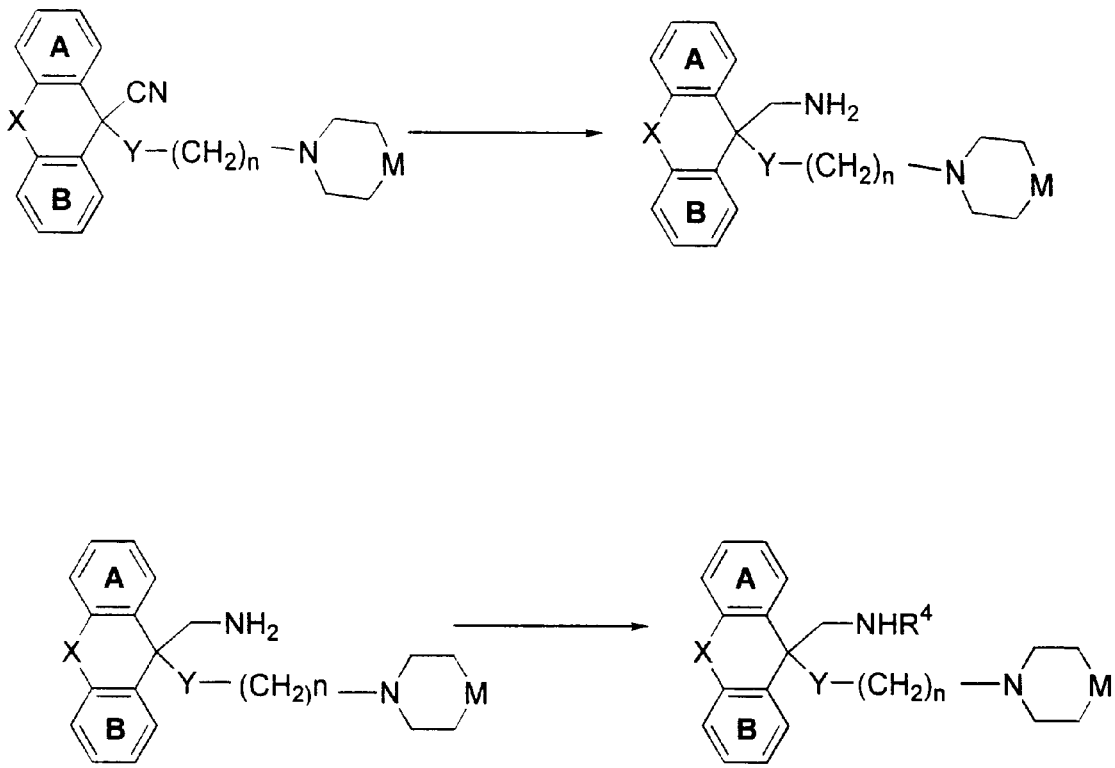
FIG. 3 is a schematic showing the preparation of the compounds represented by Structural Formula (I) and (II), wherein Z is represented by Structural Formulas (VIII) and (XIII)–(XVI) and wherein V is W$_a$.
Figure 4A:
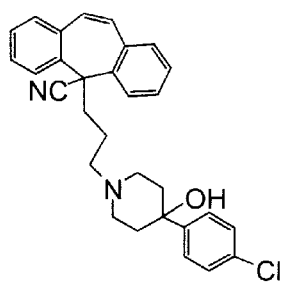
FIGS. 4A–4F show the structures of a number of exemplary compounds of the present invention.
Figure 4A:
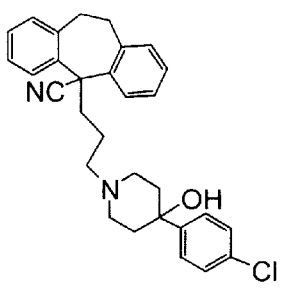
Figure 4A:
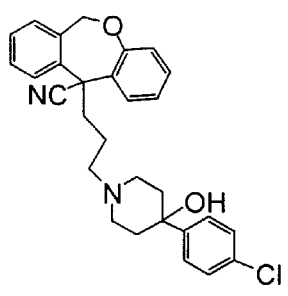
Figure 4A:
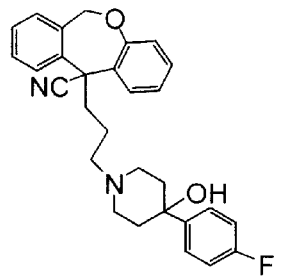
Figure 4A:
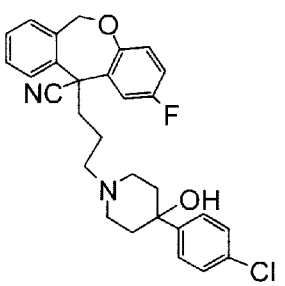
Figure 4A:
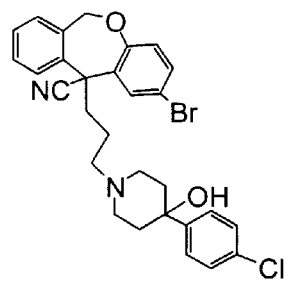
Figure 4A:
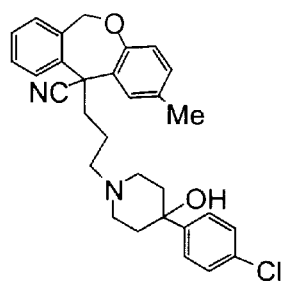
Figure 4A:
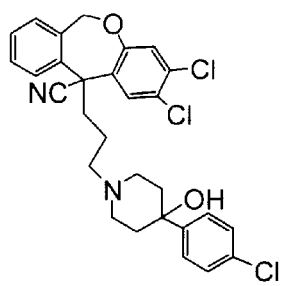
Figure 4A:
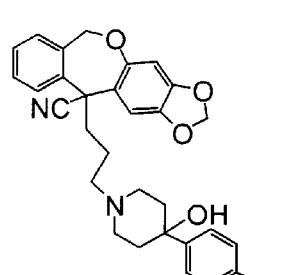
Figure 4A:
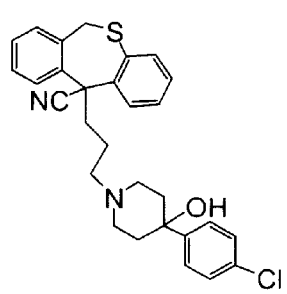
Figure 4A:
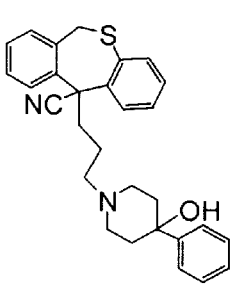
Figure 4A:
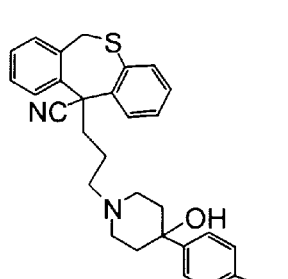
Figure 4B:
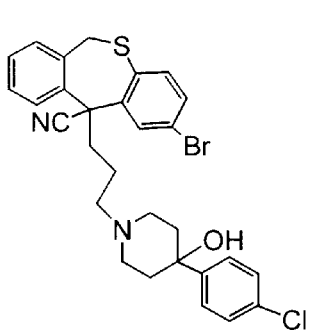
Figure 4B:
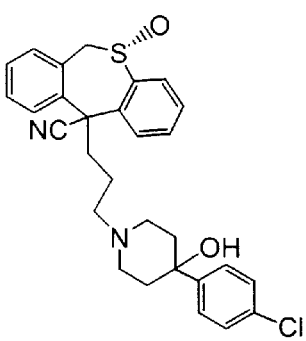
Figure 4B:
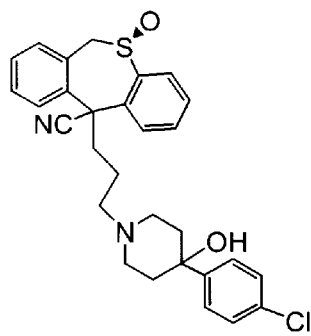
Figure 4B:
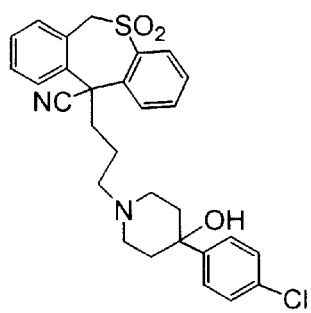
Figure 4B:
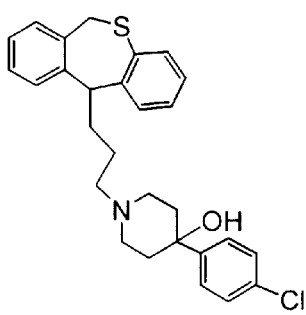
Figure 4B:
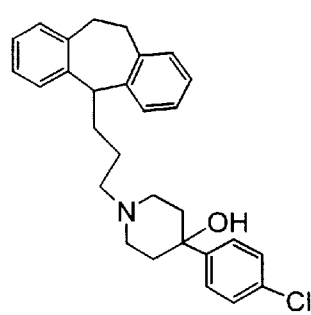
Figure 4B:
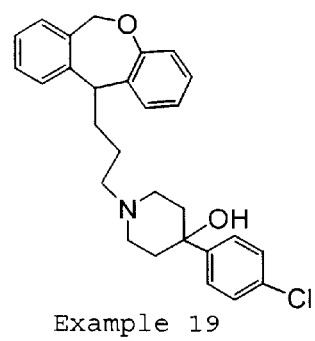
Figure 4B:
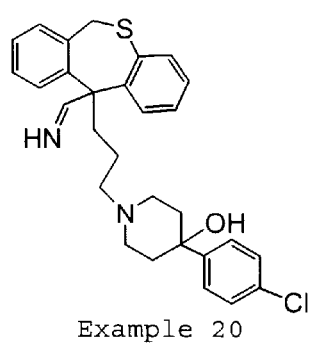
Figure 4B:
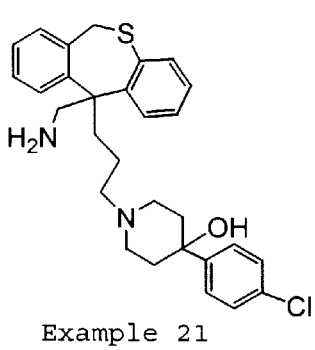
Figure 4B:
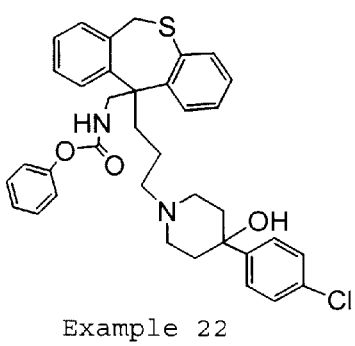
Figure 4B:
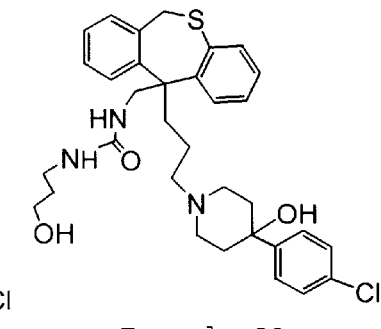
Figure 4B:
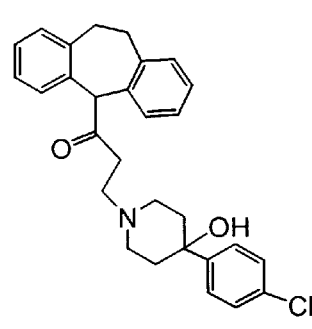
Figure 4C:
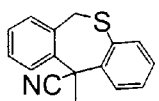
Figure 4C:
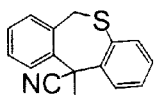
Figure 4C:
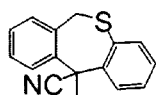
Figure 4C:
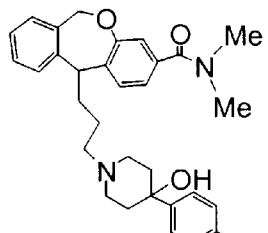
Figure 4C:
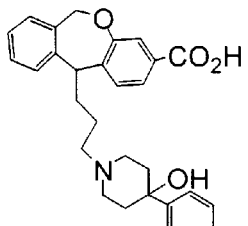
Figure 4C:
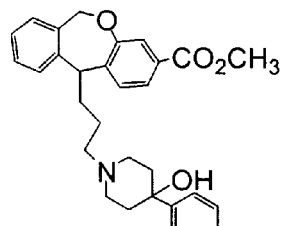
Figure 4C:
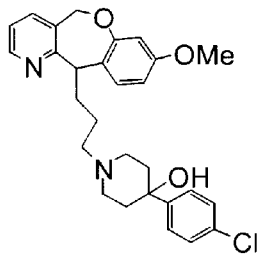
Figure 4C:
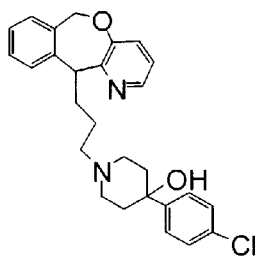
Figure 4C:
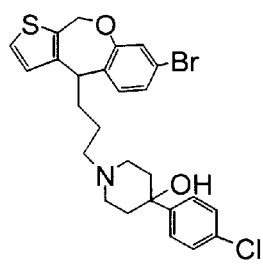
Figure 4C:
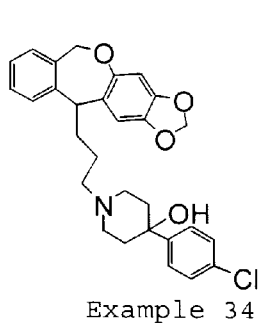
Figure 4C:
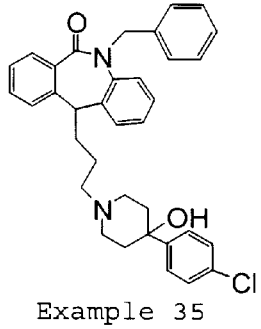
Figure 4C:
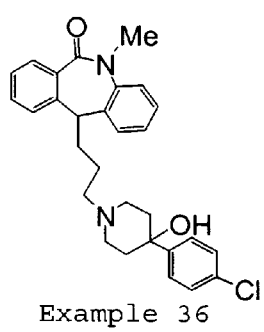
Figure 4D:
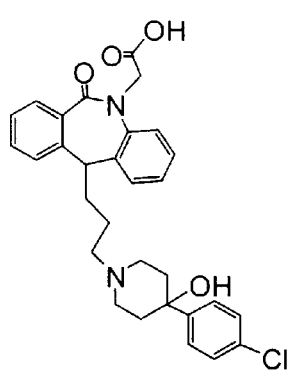
Figure 4D:
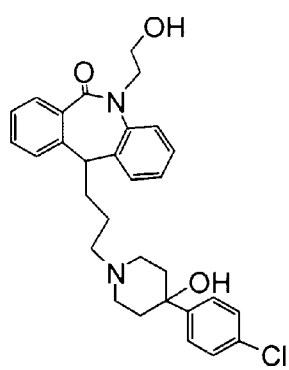
Figure 4D:
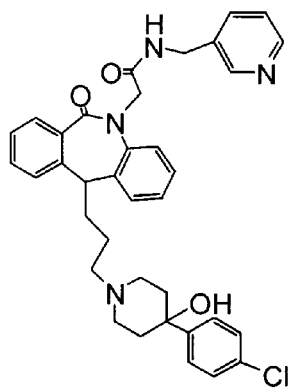
Figure 4D:
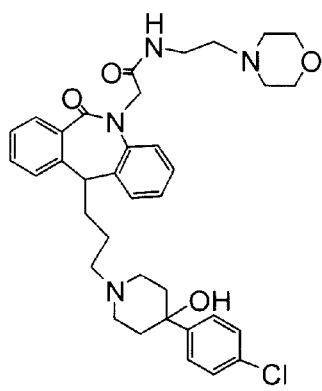
Figure 4D:
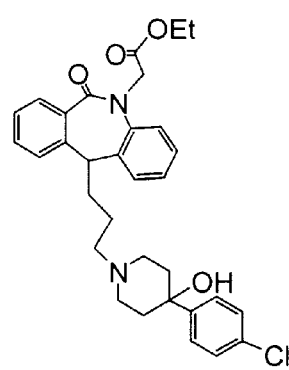
Figure 4D:
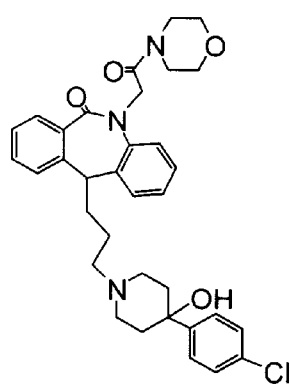
Figure 4D:
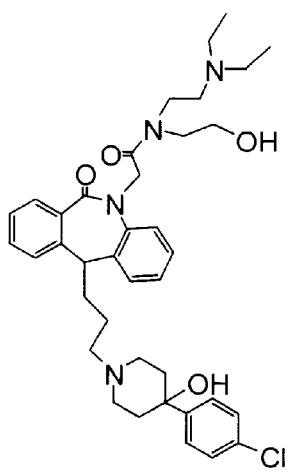
Figure 4D:
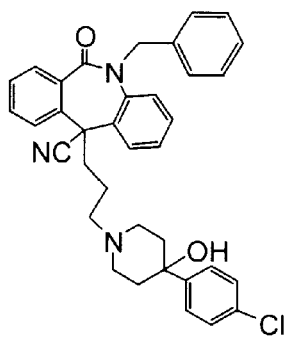
Figure 4D:
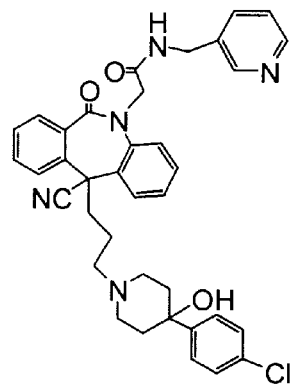
Figure 4E:
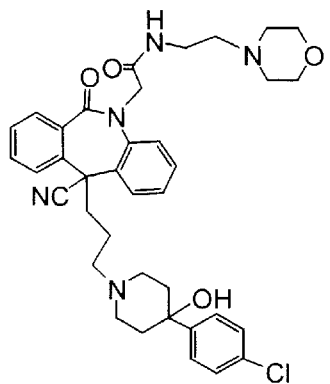
Figure 4E:
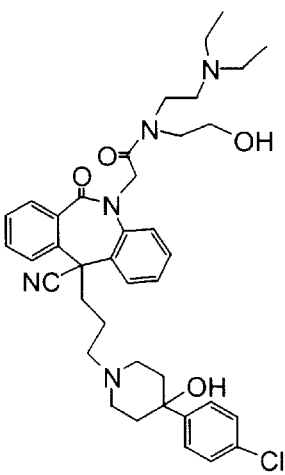
Figure 4E:
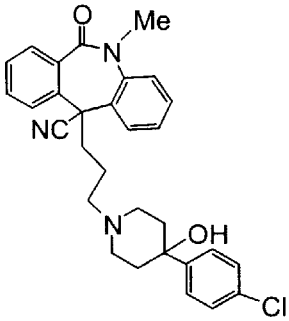
Figure 4E:
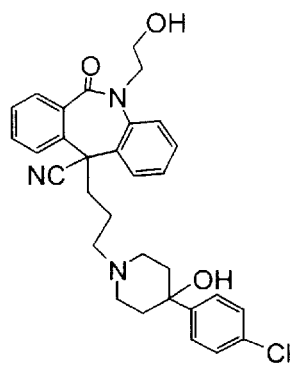
Figure 4E:
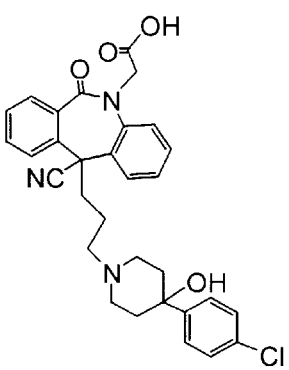
Figure 4E:
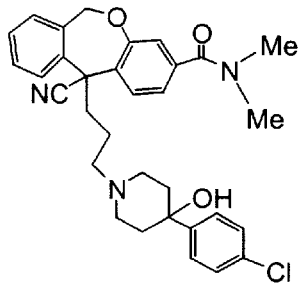
Figure 4E:
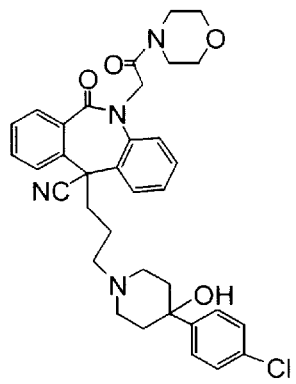
Figure 4E:
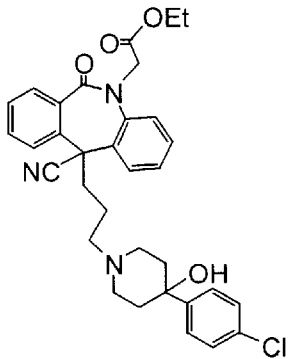
Figure 4E:
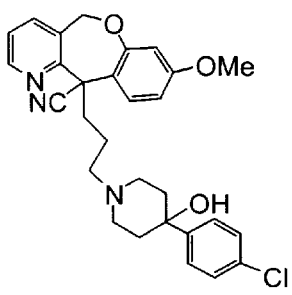
Figure 4F:
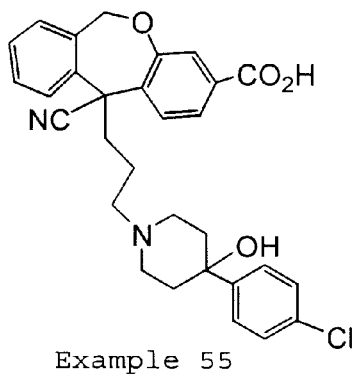
Figure 4F:
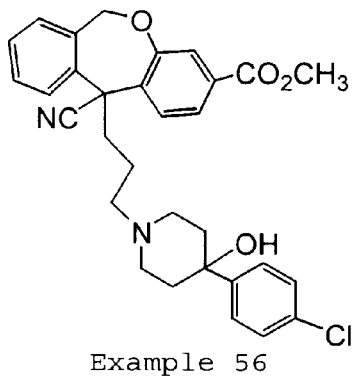
Figure 4F:
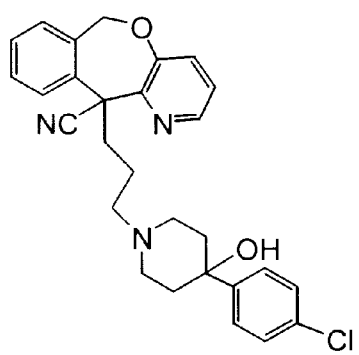
Figure 4F:
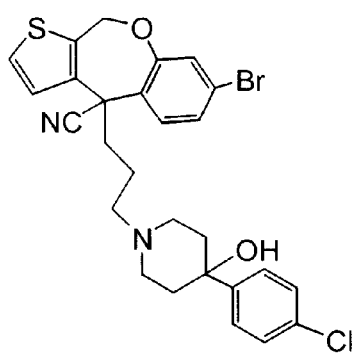
Figure 4F:
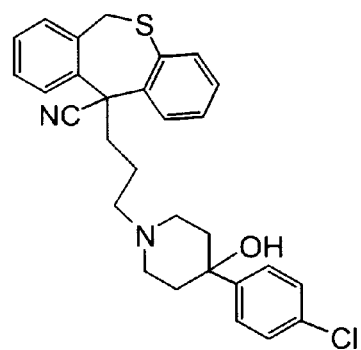

The compounds disclosed herein can be prepared accordingly to the schemes shown in FIGS. 1–3. The schemes are described in greater detail below.

FIG. 1 is a schematic showing the preparation of the compounds represented by Structural Formula (I).

$L^1$, $L^2$ and $L^3$ in FIG. 1 are suitable leaving groups such as halogen; p-toluene sulfonate, mesylate, alkoxy and phenoxy. The other symbols are as defined above.

The reduction reaction in Step 1 of FIG. 1 is performed with a reducing agent such as or sodium borohydride or lithium aluminum hydride (LAH) in an inert solvent such as methanol or tetrahydrofuran (THF. The reaction is carried out at temperatures ranging from 0° C. up to the reflux temperature and for 5 minutes to 72 h. Compounds represented by formula II in FIG. 1 can be prepared by procedures disclosed in JP 61/152673, U.S. Pat. No. 5,089,496, WO 89/10369, WO 92/20681 and WO 93/02081, the entire teachings of which are incorporated herein by reference.

A chlorination reaction in step 2 of FIG. 1 can be performed with reagents such as thionyl chloride. The reaction can be carried out in an inert solvent such as methylene chloride at 0° C. up to the reflux temperature for 5 minutes to 72 h. The hydroxy group can be also converted to other leaving groups by methods familiar to those skilled in the art.

The cyanation reaction in step 3 of FIG. 1 can be carried out using reagents such as copper cyanide, silver cyanide or sodium cyanide in an inert solvent such as benzene or toluene. Reacton temperatures range from 0° C. up to the reflux temperature for 5 minutes to 72 h. Compounds represented by Formula V in FIG. 1 can also be prepared by the procedures described in J. Med. Chem. 1994, 37, 804–810 and U.S. Pat. No. 5,672,611, the entire teachings of which are incorporated herein by reference.

The alkylation reactions in steps 4 and 5 of FIG. 1 can be carried out in a solvent such as acetone, methyl ethyl ketone, ethyl acetate, toluene, tetrahydrofuran (THF) or dimethylformamide (DMF) in the presence of a base such as potassium carbonate or sodium hydride and a catalyst such as an alkali metal iodide (when necessary). The reaction temperature can range from room temperature up to the reflux temperature and for 5 minutes to 72 h.

The product of the synthetic scheme shown in FIG. 1 can be decyanated using a reducing agent such as lithium aluminum hydride (LAH) in an inert solvent such as ether or tetrahydrofuran (THF) at 0° C. up to the reflux temperature for the solvent used for 5 minutes to 72 h.

FIG. 2 is a schematic showing the preparation of the compounds represented by Stuctural Formula (I) and II), wherein Z is represented by Structural Formulas (IV) and wherein Ring A in Z is substituted with —(CH$_2$)$_t$—COOH, —(CH$_2$)$_t$—COOR$^{20}$ or —(CH$_2$)$_t$—C(O)—NR$^{21}$R$^{22}$.

In FIG. 2, the hydrolysis reaction may be carried out in a mixture of aqueous alkali metal hydroxide solution and a solvent such as methanol, ethanol, tetrahydrofuran (THF) or dioxane at room temperature up to the reflux temperature for the solvent used for 5 minutes to 72 h. The acylation reaction can be carried out using dicyclohexylcarbodiimide (DCC) or (1-ethyl-3-(3-dimethylaminopropyl)carbodiimide (DEC) in a solvent such as tetrahydrofuran (THF), dimethylformamide (DMF) or methylene chloride in the presence of a base such as pyridine or triethylamine (when necessary) at temperatures of 0 to 100° C. for 5 minutes to 72 h.

Compounds represented by Structural Formulas (I) and (II), wherein Z is represented by Structural Formulas (XVI), X is —CO—N(R$_C$)— and R$_C$ is —(CH$_2$)$_S$—COOH, —(CH$_2$)$_S$—COOR$^{30}$ or —(CH$_2$)$_S$—C(O)—NR$^3$R$^{32}$ can be prepared by suitable modification of the scheme shown in FIG. 1. One modification utilizes the starting material shown in FIG. 1, wherein X is —CO—NH—. The amide is then alkylated with $L^3$—(CH$_2$)$_s$—COOR$^{30}$ using the alkylation procedures described above. $L^3$ is a suitable leaving group. The remainder of the synthesis is as described in FIGS. 1 and 2.

FIG. 3 is a schematic showing the preparation of the compounds represented by Structural Formula (I) and (II), wherein Z is represented by Structural Formulas (VIII) and (XIII–(XVI) and wherein V is $W_a$.

The reduction of the cyano group to an amine in FIG. 3 can be carried out using metal hydrides or by catalytic reduction processes. Suitable reducing agents include lithium aluminum hydride (LAH), diisobutyl aluminum hydride (DIBAL-H), borane-methyl sulfide complex or sodium borohydride. The reduction can be carried out in an inert solvent such as ether, tetrahydrofuran (THF), methylene chloride or methanol at −78° C. up to the reflux temperature for 5 minutes to 72 h. It is also possible to isolate the corresponding imine intermediate, which can be converted to the amine using similar reduction processes.

Although FIGS. 1–3 show the preparation of compounds in which Rings A and B are phenyl rings, analogous compounds with heteroaryl groups for Rings A and B can be prepared by using the starting materials with heteroaryl groups in the corresponding positions, which can be prepared according to methods disclosed in JP 61/152673, U.S. Pat. No. 5,089,496, WO 89/10369, WO 92/20681 and WO 93/02081.

The invention is illustrated by the following examples which are not intended to be limiting in any way.

EXEMPLIFICATION

Example 1

Preparation of 4-(4-Chlorophenyl)1-[3-(5-cyano-5H-dibenzo[a,d]cycloheptene-5-yl)propyl]piperidin-4-ol To a solution of 5H-dibenzo[a,d]cycloheptene-5-carbonitrile (described in J. Med Chem. 1994, 37, 804–810) (500mg) in DMF (10 ml) were added 60% sodium hydride (110 mg) and 1-bromo-3- chloropropane (0.30 ml) and the mixture was stirred at room temperature for 1 hours. Water and ethyl acetate were added to the reaction mixture, the organic layer was separated and washed with saturated aqueous sodium chloride, and dried over magnesium sulfate. The solvent was distilled off under reduced pressure to give 5-(3-chloropropyl-5H-dibenzo[a,d]cycloheptene-5-carbonitrile. Without purification, to a solution obtained chloride in DMF (10 ml) were added 4-(4-chlorophenyl)-4-hydroxypiperidine (650 mg), potassium carbonate (950 mg), and potassium iodide (50 mg) and the mixture was stirred at 70° C. for 24 hours. Water and ethyl acetate were added to the reaction mixture, the organic layer was separated and washed with saturated aqueous sodium chloride, and dried over magnesium sulfate. The solvent was distilled off under reduced pressure. The residue was purified by silica gel chromatography eluting with ethyl acetate-hexane (1:1) to give the titled compound (700 mg). $^1$H-NMR (CDCl$_3$) d: 1.22–1.34(2H,m), 1.60–1.80(3H,m), 1.93–1.99(2H,m), 2.16–2.28(6H,m), 2.56–2.60(2H,m), 6.98(2H,s), 7.25–7.47 (10H,m), 8.00–8.03(2H,m). MS m/z: 469(M+1)

Example 2

Preparation of 4-(4-Chlorophenyl)-1-[3-(5-cyano-10,11-dihydro-5H-dibenzo[a,d]cycloheptene-5-yl) propyl]piperidin-4-ol Following the procedure of example 1, but replacing 5H-dibenzo[a,d]cycloheptene-5-carbonitrile with 10,11-dihydro-5H-dibenzo[a,d]cycloheptene-5-carbonitrile, the titled compound was prepared. $^1$H-NMR (CDCl$_3$) d: 1.43–1.49(2H,m), 1.61–1.66(2H,m), 1.93–2.02(3H,m), 2.24–2.32(4H,m), 2.48–2.62(4H,m), 2.96–3.06(2H,m), 3.35–3.45(2H,m), 7.11–7.41(10H,m), 7.93–7.97(2H,m). MS m/z: 471(M+1)

Example 3

Preparation of 4-(4-Chlorophenyl)-1-[3-(11-cyano-6,11-dihydrodibenz[b,e]oxepin-11-yl)propyl] piperidin-4-ol Following the procedure of example 1, but replacing 5H-dibenzo[a,d]cycloheptene-5-carbonitrile with 6,11-dihydrodibenz[b,e]oxepin-11-carbonitrile, the titled compound was prepared. $^1$H-NMR (CDCl$_3$) d: 1.37–1.68(5H, m), 1.99–2.09(2H,m), 2.24–2.50(5H,m), 2.65–2.69(2H,m), 2.78–2.85(1H,m), 5.03(1H,d), 5.45(1H,d), 7.02–7.43(10H, m), 7.82–7.86(1H,m), 7.95–8.00(1H,m). MS m/z: 473(M+1)

Example 4

Preparation of 1-[3-(11-Cyano-6,11-dihydrodibenz [b,e]oxepin-11-yl)propyl]-4-(4-fluorophenyl) piperidin-4-ol Following the procedure of example 3, but replacing 4-(4-chlorophenyl)-4-hydroxypiperidine with 4-(4-fluorophenyl)-4-hydroxypiperidine, the titled compound was prepared. $^1$H-NMR (CDCl$_3$) d: 1.40–1.68(4H,m), 1.88–2.08(3H,m), 2.29–2.50(5H,m), 2.63–2.67(2H,m), 2.77–2.84(1H,m), 5.03(1H,d), 5.44(1H,d), 6.95–7.46(10H, m), 7.81–7.85(1H,m), 7.94–7.99(1H,m). MS m/z: 457(M+1)

Example 5

Preparation of 4-(4-Chlorophenyl)-1-[3-(11-cyano-6,11-dihydro-2-fluorodibenz[b,e]oxepin-11-yl)prop yl]piperidin-4-ol Following the procedure of example 1, but replacing 5H-dibenzo[a,d]cycloheptene-5-carbonitrile with 6,11-dihydro-2-fluorodibenz[b,e]oxepin-11-carbonitrile, the titled compound was prepared. $^1$H-NMR (CDCl$_3$) d: 1.37–1.69(5H,m), 1.98–2.09(2H,m), 2.25–2.48(5H,m), 2.65–2.70(2H,m), 2.78–2.87(1H,m), 5.01(1H,d), 5.42(1H, d), 6.99–7.11(3H,m), 7.25–7.43(6H,m), 7.54–7.59(1H,m), 7.92–7.95(1H,m). MS m/z: 491(M+1)

Example 6

Preparation of 1-[3-(2-Bromo-11-cyano-6,11-dihydrodibenz[b,e]oxepin-11-yl)propyl]-4-(4-chlorophenyl)piperidin-4-ol Following the procedure of example 1, but replacing 5H-dibenzo[a,d]cycloheptene-5-carbonitrile with 2-bromo-6,11-dihydrodibenz[b,e]oxepin-11-carbonitrile, the titled compound was prepared. $^1$H-NMR (CDCl$_3$) d: 1.37–1.69 (5H,m), 1.97–2.09(2H,m), 2.24–2.48(5H,m), 2.66–2.85(3H, m), 5.00(1H,d), 5.43(1H,d), 6.97–7.02(2H,m), 7.24–7.46 (7H,m), 7.91–7.95(2H,m). MS m/z: 551, 553(M+1)

Example 7

Preparation of 4-(4-Chlorophenyl)-1-[3-(11-cyano-6,11-dihydro-2-methyldibenz[b,e]oxepin-11-yl) propyl]piperidin-4-ol Following the procedure of example 1, but replacing 5H-dibenzo[a,d]cycloheptene-5-carbonitrile with 6,11-dihydro-2-methyldibenz[b,e]oxepin-11-carbonitrile, the titled compound was prepared. $^1$H-NMR (CDCl$_3$) d: 1.40–1.70(5H,m), 1.98–2.09(2H,m), 2.25–2.52(8H,m), 2.68–2.73(2H,m), 2.81–2.90(1H,m), 5.00(1H,d), 5.44(1H, d), 6.98–7.43(9H,m), 7.63(1H,d), 7.94–7.98(1H,m). MS m/z: 487(M+1)

Example 8

Preparation of 4-(4-Chlorophenyl)-1-[3-(11-cyano-3,4-dichloro-6,11-dihydro-dibenz[b,e]oxepin-11-yl) propyl]piperidin-4-ol Following the procedure of example 1, but replacing 5H-dibenzo[a,d]cycloheptene-5-carbonitrile with 3,4-dichloro-6,11-dihydrodibenz[b,e]oxepin-1-carbonitrile, the titled compound was prepared. $^1$H-NMR (CDCl$_3$) d: 1.40–1.71(5H,m), 2.00–2.10(2H,m), 2.28–2.50(5H,m), 2.65–2.85(3H,m), 5.04(1H,d), 5.46(1H,d), 6.99–7.03(1H, m), 7.26–7.44(7H,m), 7.91–7.95(2H,m). MS m/z: 541(M+1)

Example 9

Preparation of 4-(4-Chlorophenyl)-1-[3-(11-cyano-6,11-dihydro-2,3-methylenedioxydibenz[b,e]oxepin-11-yl)propyl]piperidin-4-ol Following the procedure of example 1, but replacing 5H-dibenzo[a,d]cycloheptene-5-carbonitrile with 6,11- dihydro-2,3-methylenedioxydibenz[b,e]oxepin-11-carbonitrile, the titled compound was prepared. ¹H-NMR (CDCl₃) d: 1.60–1.90(5H,m), 2.30–2.50(2H,m), 2.80–3.30 (8H,m), 5.05(1H,d), 5.45(1H,d), 6.02(2H,brd), 6.68(1H,s), 6.97–7.01(1H,m), 7.26–7.43(7H,m), 7.83–7.87(2H,m). MS m/z: 517(M+1)

Example 10

Preparation of 4-(4-Chlorophenyl)-1-[3-(11-cyano-6,11-dihydrodibenzo[b,e]thiepin-11-yl)propyl] piperidin-4-ol Following the procedure of example 1, but replacing 5H-dibenzo[a,d]cycloheptene-5-carbonitrile with 6,11-dihydrodibenzo[b,e]thiepin-11-carbonitrile, the titled compound was prepared. ¹H-NMR (CDCl₃) d: 1.63–1.76(5H, m), 2.03–2.16(2H,m), 2.37–2.52(4H,m), 2.72–2.85(3H,m), 3.03–3.10(1H,m), 4.10(1H,d), 4.54(1H,d), 7.13–7.44(10H, m), 7.81–7.87(2H,m). MS m/z: 489(M+1)

Example 11

Preparation of 1-[3-(11-Cyano-6,11-dihydrodibenzo [b,e]thiepin-11-yl)propyl]-4-phenylpiperidin-4-ol Following the procedure of example 10, but replacing 4-(4-chlorophenyl)-4-hydroxypiperidine with 4-hydroxy-4-phenylpiperidine, the titled compound was prepared. ¹H-NMR (CDCl₃) d: 1.63–1.77(5H,m), 2.02–2.16(2H,m), 2.37–2.52(4H,m), 2.72–2.85(3H,m), 3.03–3.10(1H,m), 4.10 (1H,d), 4.55(1H,d), 7.13–7.52(10H,m), 7.81–7.88(2H,m). MS m/z: 455(M+1)

Example 12

Preparation of 4-(4-Bromophenyl)-1-[3-(11-cyano-6,11-dihydrodibenzo[b,e]thiepin-11-yl)propyl] piperidin-4-ol Following the procedure of example 10, but replacing 4-(4-chlorophenyl)-4-hydroxypiperidine with 4-(4-bromophenyl)-4- hydroxypiperidine, the titled compound was prepared. ¹H-NMR (CDCl₃) d: 1.64–1.82(5H,m), 2.02–2.12(2H,m), 2.32–2.48(4H,m), 2.69–2.85(3H,m), 2.99–3.09(1H,m), 4.07(1H,d), 4.50(1H,d), 7.11–7.46(10H, m), 7.79–7.86(2H,m). MS m/z: 533, 535(M+1)

Example 13

Preparation of 1-[3-(2-Bromo-11-cyano-6,11-dihydrodibenzo[b,e]thiepin-11-yl)propyl]-4-(4-chlorophenyl)piperidin-4-ol Following the procedure of example 1, but replacing 5H-dibenzo[a,d]cycloheptene-5-carbonitrile with 2-bromo-6,11-dihydrodibenzo[b,e]thiepin-11-carbonitrile, the titled compound was prepared. ¹H-NMR (CDCl₃) d: 1.63–1.78 (5H,m), 2.03–2.14(2H,m), 2.35–2.52(4H,m), 2.72–2.80(3H, m), 3.00–3.10(1H,m), 4.15(1H,brd), 4.50(1H,d), 7.07–7.45 (10H,m), 7.73–7.81(1H,m), 7.95(1H,d). MS m/z: 567, 569 (M+1)

Example 14, 15

Preparation of 4-(4-Chlorophenyl)-l-[3-(11- cyano-6,11-dihydro-5-oxodibenzo[b,e]thiepin-11-yl)propyl] piperidin-4-ol Following the procedure of example 1, but replacing 5H-dibenzo[a,d]cycloheptene-5-carbonitrile with 6,11-dihydro-5-oxodibenzo[b,e]thiepin-11-carbonitrile, the titled compound was prepared. The diastereomers were separated by silica gel chromatography. isomer 1H-NMR (CDCl₃) d: 1.20–1.35(1H,m), 1.63–1.69(4H,m), 2.04–2.84(10 H,m), 4.21(1H,d), 4.31(1H,d), 7.18–7.65(9H,m), 8.03–8.13(3H, m). MS m/z: 505(M+1) isomer 2 ¹H-NMR (CDCl₃) d: 1.25–1.38(1H,m), 1.65–2.15(6H,m), 2.28–2.82(8H,m), 4.65 (1H,d), 4.82(1H,d), 7.27–7.56(9H,m), 7.92–8.00(3H,m). MS m/z: 505(M+1)

Example 16

Preparation of 4-(4-Chlorophenyl)-1-[3-(11-cyano-6,11-dihydro-5,5-dioxodibenzo[b,e]thiepin-11-yl) propyl]piperidin-4-ol Following the procedure of example 1, but replacing 5H-dibenzo[a,d]cycloheptene-5-carbonitrile with 6 11-dihydro-5,5-dioxodibenzo[b,e]thiepin-11-carbonitrile, the titled compound was prepared. ¹H-NMR (CDCl₃) d: 1.40–2.72(14H,m), 3.08–3.22(1H,m), 4.58(1H,d), 5.58(1H, d), 7.29–7.58(9H,m), 7.99–8.13(3H,m). MS m/z: 521(M+1)

Example 17

Preparation of 4-(4-Chlorophenyl)-1-[3-(6,11-dihydrodibenzo[b,e]thiepin-11-yl)propyl]piperidin-4-ol To a solution of 4-(4-chlorophenyl)-1-[3-(11-cyano-6,11-dihydrodibenzo[b,e]thiepin-11-yl)propyl]piperidin-4-ol (430mg) in THF 10ml) was added 1M lithium aluminum hydride THF solution (1.5 ml) and the mixture was heated to reflux for 3 hours. The reaction mixture was cooled with ice, water (0.06 ml), then 15% aqueous sodium hydroxide (0.06 ml), then water (0.18 ml) were added carefully. The granular salt was filtered off and the filtrate was distilled off under reduced pressure. The residue was purified by silica gel chromatography eluting with ethyl acetate-hexane (1:1) to give the titled compound (280mg). ¹H-NMR (CDCl₃) d: 1.55–1.80(4H,m), 2.03–2.16(2H,m), 2.25–2.52(6H,m), 2.72–2.80(2H,m), 3.90(1H,brs), 4.48(1H,brt), 4.68(1H,brs), 6.96–7.45(12H,m). MS m/z: 464(M+1)

Example 18

Preparation of 4-(4-Chlorophenyl)-1-[3-(10,11-dihydro-5H-dibenzo[a,d]cycloheptene-5-yl)propyl] piperidin-4-ol Following the procedure of example 17, but replacing 4-(4-chlorophenyl)-1-[3-(11-cyano-6,11-dihydrodibenzo[b, e]thiepin-11-yl)propyl]piperidin-4-ol with 4-(4-chlorophenyl)-1-[3-(5-cyano-10,11-dihydro-5H-dibenzo[a, d]cycloheptene-5-yl)propyl]piperidin-4-ol, the titled compound was prepared. ¹H-NMR (CDCl₃) d: 1.40–1.58 (2H,m), 1.62–1.71(2H,m), 1.98–2.20(4H,m), 2.30–2.42(4H, m), 2.67–2.78(2H,m), 2.95–3.08(2H,m), 3.30–3.44(2H,m), 4.01(1H,t), 7.10–7.46(12H,m). MS m/z: 446(M+1)

Example 19

Preparation of 4-(4-Chlorophenyl)-1-[3-(6,11-dihydrodibenz[b,e]oxepin-11-yl)propyl]piperidin-4-ol Following the procedure of example 17, but replacing 4-(4-chlorophenyl)-1-[3-(11-cyano-6,11-dihydrodibenzo[b, e]thiepin-11-yl)propyl]piperidin-4-ol with 4-(4-chlorophenyl)-1-[3-(11-cyano-6,11-dihydrodibenz[b,e]ox epin-11-yl)propyl]piperidin-4-ol, the titled compound was prepared. $^1$H-NMR (CDCl$_3$) d: 1.36–1.49(2H,m), 1.58–1.67 (2H,m), 1.95–2.33(8H,m), 2.63–2.68(2H,m), 3.74(1H,t), 4.95(1H,d), 5.48(1H,d), 6.95–7.39(12H,m). MS m/z: 448 (M+1)

Example 20

Preparation of 4-(4-Chlorophenyl)-1-[3-(6,11-dihydro-11-iminodibenzo[b,e]thiepin-11-yl)propyl] piperidin-4-ol To a solution of 4-(4-chlorophenyl)-1-[3-(11-cyano-6,11-dihydrodibenzo[b,e]thiepin-11-yl)propyl]piperidin-4-ol (1.92 g) in dichloromethane (30 ml) at −78° C. was added 1M diisobutyl aluminum hydride dichloromethane solution (10 ml). The reaction mixture was warmed to room temperature, and stirred for 30 minutes. Water and dichloromethane were added to the reaction mixture, the organic layer was separated and washed with saturated aqueous sodium chloride, and dried over magnesium sulfate. The solvent was distilled off under reduced pressure. The residue was purified by silica gel chromatography eluting with ethyl acetate to give the titled compound (1.16 g). $^1$H-NMR (CDCl$_3$) d: 1.65–1.80(5H,m), 2.02–2.18(2H,m), 2.45–2.60 (6H,m), 2.78–2.86(2H,m), 3.82(1H,d), 4.25(1H,d), 7.05–7.45(12H,m), 8.28(1H,brs). MS m/z: 491(M+1)

Example 21

Preparation of 4-(4-Chlorophenyl)-1-[3-(11-aminomethyl-6,11-dihydrodibenzo[b,e]thiepin-11-yl) propyl]piperidin-4-ol To a solution of 4-(4-chlorophenyl)-1-[3-(6,11-dihydro-11-iminodibenzo[b,e]thiepin-11-yl)propyl]piperidin-4-ol (600 mg) in methanol (15 ml) was sodium borohydride (220 mg), and the mixture was stirred at room temperature for 10 hours. The solvent was distilled off under reduced pressure. Water and ethyl acetate were added to the reaction mixture, the organic layer was separated and washed with saturated aqueous sodium chloride, and dried over magnesium sulfate. The solvent was distilled off under reduced to give the titled compound (600 mg). MS m/z:493 (M+1)

Example 22

Preparation of Phenyl N-[2-[3-[4-(4-chlorophenyl)-4-hydroxypiperidino]propyl]-2-(6,11-dihydrodibenzo[b,e]thiepin-11-yl)ethyl]carbamate To a solution of 4-(4-chlorophenyl)-1-[3-(11-aminomethyl-6,11-dihydrodibenzo[b,e]thiepin-11-yl) propyl]piperidin-4-ol (610 mg) in THF (20 ml) was triethylamine (0.2 ml) and phenyl chlorocarbonate (0.16 ml) at 0° C., and the mixture was stirred for 1 hours. Water and ethyl acetate were added to the reaction mixture, the organic layer was separated and washed with saturated aqueous sodium chloride, and dried over magnesium sulfate. The solvent was distilled off under reduced pressure. The residue was purified by silica gel chromatography eluting with ethyl acetate to give the titled compound (400 mg). $^1$H-NMR (CDCl$_3$) d: 1.40–2.90(15H,m), 4.05–4.12(2H,m), 4.38(1H,d), 4.50–4.60(1H,m), 5.98(1H,brs), 6.96–7.54(17H,m). MS m/z: 613(M+1)

Example 23

Preparation of 1-[2-[3-[4-(4-chlorophenyl)-4-hydroxypiperidino]propyl]-2-(6,11-dihydrodibenzo [b,e]thiepi n-11-yl)ethyl]-3-(hydroxypropyl)urea To a solution phenyl N-[2-[3-[4-(4-chlorophenyl)-4-hydroxypiperidino]propyl]-2-(6,11-dihydrodibenzo[b,e] thiepin-11-yl)ethyl]carbamate (300 mg) in DMF (10 ml) were added 3-amino-1-propanol (70 mg), potassium carbonate (130 mg) and the mixture was stirred at room temperature for 16 hours. Water and ethyl acetate were added to the reaction mixture, the organic layer was separated and washed with saturated aqueous sodium chloride, and dried over magnesium sulfate. The solvent was distilled off under reduced pressure. The residue was purified by silica gel chromatography eluting with ethyl acetate-methanol (9:1) to give the titled compound (200 mg). $^1$H-NMR (CDCl$_3$) d: 1.40–1.70(6H,m), 2.01–2.08(2H,m), 2.30–2.63(8H,m), 3.12 (2H,q), 3.42(2H,t), 4.00–4.12(2H,m), 4.22–4.28(2H,m), 4.82(1H,brt), 4.99(1H,brs), 6.98–7.45(12H,m).MS m/z: 594 (M+1)

Example 24

Preparation of 4-(4-Chlorophenyl)-1-[3-(10,11-dihydro-5H-dibenzo[a,d]cycloheptene-5-yl)-3-propioyl]piperidin-4-ol To a solution 10,11-dihydro-5H-dibenzo[a,d] cycloheptene-5-carbonitrile (500 mg) in THF (5 ml) was added 1.6M n-butyl lithium hexane solution (1.8 ml) at 0° C. The mixture was warmed to room temperature, and stirred for 20 minutes. To the reaction mixture cooled to 0° C. was added ethyl 3-(4-(4-chlorophenyl)-4-hydroxypiperidine-1-yl)propionate (310 mg) dropwise as THF solution (2 ml), and the mixture was warmed to room temperature, and stirred for 30 minutes. Water and ethyl acetate were added to the reaction mixture, the organic layer was separated and washed with saturated aqueous sodium chloride, and dried over magnesium sulfate. The solvent was distilled off under reduced pressure. The residue was purified by silica gel chromatography eluting with ethyl acetate-hexane (1:1) to give the titled compound (380 mg). $^1$H-NMR (CDCl$_3$) d: 1.57–1.62(2H,m), 1.91–2.01(3H,m), 2.27–2.84(10H,m), 3.30–3.44(2H,m), 4.65(1H,s), 7.10–7.38(12H,m). MS m/z: 460(M+1)

Examples 28–59 can be prepared by methods set forth in the schemes in FIGS. 1–3 and the procedures described above.

Example 60

Membrane Preparations for Chemokine Binding and Binding Assays

Membranes were prepared from THP-1 cells (ATCC #TIB202). Cells were harvested by centrifugation, washed twice with PBS (phosphate-buffered saline), and the cell pellets were frozen at −70 to −85° C. The frozen pellet was thawed in ice-cold lysis buffer consisting of 5 mM HEPES (N-2-hydroxyethylpiperazine-N'-2-ethane-sulfonic acid) pH 7.5, 2 mM EDTA (ethylenediaminetetraacetic acid), 5 µg/ml each aprotinin, leupeptin, and chymostatin (protease inhibitors), and 100 µg/ml PMSF (phenyl methane sulfonyl fluoride—also a protease inhibitor), at a concentration of 1 to 5×10$^7$ cells/ml. This procedure results in cell lysis. The suspension was mixed well to resuspend all of the frozen cell pellet. Nuclei and cell debris were removed by centrifugation of 400×g for 10 minutes at 4° C. The supernatant was transferred to a fresh tube and the membrane fragments were collected by centrifugation at 25,000×g for 30 minutes at 4° C. The supernatant was aspirated and the pellet was resuspended in freezing buffer consisting of 10 mM HEPES pH 7.5, 300 mM sucrose, 1 µg/ml each aprotinin, leupeptin, and chymostatin, and 10 µg/ml PMSF (approximately 0.1 ml per each $10^8$ cells). All clumps were resolved using a minihomogenizer, and the total protein concentration was determined using a protein assay kit (Bio-Rad, Hercules, Calif., cat #500-0002). The membrane solution was then aliquoted and frozen at −70 to −85° C. until needed.

Binding Assays utilized the membranes described above. Membrane protein (2 to 20 μg total membrane protein) was incubated with 0.1 to 0.2 nM $^{125}$I-labeled RANTES or MIP-1α with or without unlabeled competitor (RANTES or MIP-1α) or various concentrations of compounds. The binding reactions were performed in 60 to 100 μl of a binding buffer consisting of 10 mM HEPES pH 7.2, 1 mM $CaCl_2$, 5 mM $MgCl_2$, and 0.5% BSA (bovine serum albumin), for 60 min at room temperature. The binding reactions were terminated by harvesting the membranes by rapid filtration through glass fiber filters (GF/B or GF/C, Packard) which were presoaked in 0.3% polyethyleneimine. The filters were rinsed with approximately 600 μl of binding buffer containing 0.5 M NaCl, dried, and the amount of bound radioactivity was determined by scintillation counting in a Topcount beta-plate counter.

The activities of test compounds are reported in the Table below as $IC_{50}$ values or the inhibitor concentration required for 50% inhibition of specific binding in receptor binding assays using $^{125}$I-RANTES or $^{125}$MIP-1α as ligand and THP-1 cell membranes. Specific binding is defined as the total binding minus the non-specific binding; non-specific binding is the amount of cpm still detected in the presence of excess unlabeled Rantes or $^{125}$MIP-1α.

TABLE

| BIOLOGICAL DATA | |
|---|---|
| Example | $IC_{50}$ (μM) |
| 1 | 0.088 |
| 2 | 0.052 |
| 3 | 0.11 |
| 4 | 0.39 |
| 5 | 0.19 |
| 6 | 0.30 |
| 7 | 0.38 |
| 10 | 0.097 |
| 11 | 11 |
| 12 | 0.099 |
| 13 | 0.38 |
| 14 | 0.28 |
| 15 | 0.61 |
| 16 | 0.079 |
| 17 | 0.070 |
| 18 | 0.055 |
| 19 | 0.059 |
| 22 | 0.69 |
| 23 | 2.2 |
| 24 | 0.16 |
| 25 | 0.13 |
| 26 | 0.61 |
| 27 | 0.48 |

Equivalents

Those skilled in the art will be able to recognize, or be able to ascertain, using no more than routine experimentation, many equivalents to the specific embodiments of the invention described herein. Such equivalents are intended to be encompassed by the following claims.

What is claimed is:

1. A compound represented by the following structural formula:

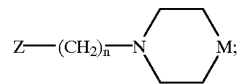

or physiologically acceptable salt thereof, wherein:
Z is a tricyclic ring system represented by:

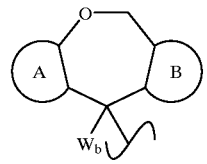

wherein Ring A is a carbocyclic aromatic ring or a heteroaromatic ring, Ring B is a heteroaromatic ring and each ring in Z is independently substituted or unsubstituted;
$W_b$ is —H, —CN, —$CH_2$—$NR^{11}R^{12}$, —$CH_2$—$OR^{11}$, —$CH_2$—NH—CO—$NR^{11}R^{12}$ or —$CH_2$—O—CO—$NR^{11}R^{12}$;
$R^{11}$ and $R^{12}$ are each independently —H, an aliphatic group, a substituted aliphatic group, an aromatic group, a substituted aromatic group, —NHC(O)—O-(aliphatic group), —NHC(O)—O-(aromatic group) or $R^{11}$ and $R^{12}$ taken together with the nitrogen atom to which they are bonded form a non-aromatic heterocyclic ring;
n is an integer from one to about five;
M is >$NR_2$ or >$CR_1R_2$;
$R_1$ is —H, —OH, an aliphatic group, —O-(aliphatic group), —SH or —S-(aliphatic group);
$R_2$ is an aliphatic group, a substituted aliphatic group, an aromatic group, a substituted aromatic group, a benzylic group, a substituted benzylic group, a non-aromatic heterocyclic group or a substituted non-aromatic heterocyclic group.

2. The compound of claim 1 wherein n is three.

3. The compound of claim 1 wherein $R_2$ is a $C_2$–$C_8$ aliphatic group, a substituted aliphatic group, an aromatic group, a substituted aromatic group, a benzylic group, a substituted benzylic group, a non-aromatic heterocyclic group or a substituted non-aromatic heterocyclic group.

4. The compound of claim 1 wherein $R_2$ is a substituted aromatic group.

5. The compound of claim 1 wherein M is >$CR_1R_2$.

6. The compound of claim 5 wherein R1 is —OH and $R_2$ is 4-chlorophenyl.

7. A compound represented by the following structural formula:

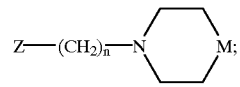

and physiologically acceptable salts thereof, wherein:
M is >$NR_2$ or $CR_1R_2$;
$R_1$ is —H, —OH, an aliphatic group, —O-(aliphatic group), —SH or —S-(aliphatic group);
$R_2$ is an aliphatic group, a substituted aliphatic group, an aromatic group, a substituted aromatic group, a benzylic group, a substituted benzylic group, a non-aromatic heterocyclic group or a substituted non-aromatic heterocyclic group;

n is an integer from one to about five;

Z is

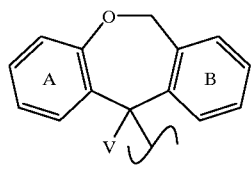

V is —H, an electron withdrawing group —CH₂—NR¹¹R¹², —CH₂—OR¹¹, —CH₂—NH—CO—NR¹¹R¹² or —CH₂—O—CO—NR¹¹R¹²;

R¹¹ and R¹² are each independently —H, an aliphatic group, a substituted aliphatic group, an aromatic group, a substituted aromatic group, —NHC(O)—O-(aliphatic group), —NHC(O)—O-(aromatic soup) or R¹¹ and R¹² taken together with the nitrogen atom to which they are bonded form a non-aromatic heterocyclic ring; and Ring A and Ring B are independently substituted or unsubstituted.

8. The compound of claim 7 wherein [W] V is —CN.

9. The compound of claim 8 wherein R₁ is —OH.

10. The compound of claim 9 wherein M is >C(OH)R₂ and n is three.

11. The compound of claim 10 wherein R₂ is 4-chlorophenyl.

12. The compound of claim 10 wherein R₂ is a substituted or unsubstituted aromatic group.

13. The compound of claim 7 wherein n is three.

14. The compound of claim 7 wherein R₂ is a C₂-C₈ aliphatic group, a substituted aliphatic group, an aromatic group, a substituted aromatic group, a benzylic group, a substituted benzylic group, a non-aromatic heterocyclic group or a substituted non-aromatic heterocyclic group.

15. A compound represented by the following structural formula:

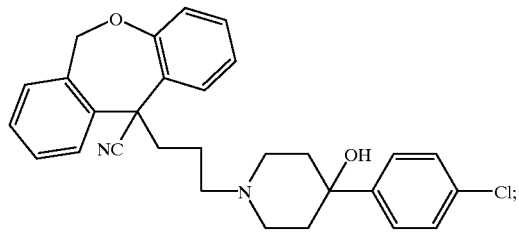

or physiologically acceptable salt thereof.

16. A compound represented by the following structural formula:

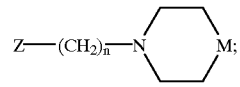

or physiologically acceptable salt thereof, wherein:

Z is represented by:

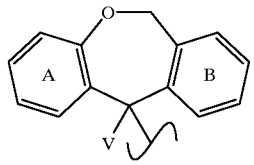

wherein V is —H, an electron withdrawing group, —CH₂—NR¹¹R¹², —CH₂—OR¹¹, —CH₂—NH—CO—NR¹¹R¹² or —CH₂—O—CO—NR¹¹R¹²;

R¹¹ and R¹² are each independently —H, an aliphatic group, a substituted aliphatic group, an aromatic group, a substituted aromatic group, —NHC(O)—O-(aliphatic group), —NHC(O)—O-(aromatic group) or R¹¹ and R¹² taken together with the nitrogen atom to which they are bonded form a non-aromatic heterocyclic ring;

n is an integer from 2–5;

Ring A or Ring B is substituted with R₈ and R₉, wherein R₈ and R₉ are independently a halogen, alkoxy or alkyl, or, taken together with Ring A, form a naphthyl group; and M is >N(alkanoyl), >N(aroyl), >N(aralkoyl), >N(alkyl), >N(aralkyl), >N(cycloalkyl), >C(OH)(aryl), >C(OH)(substituted aryl) or >CH(heteroaryl).

17. The compound of claim 16 wherein n is three.

18. The compound of claim 16 wherein M is >C(OH)(substituted aryl).

19. The compound of claim 18 wherein said substituted aryl is 4-halophenyl.

* * * * *

UNITED STATES PATENT AND TRADEMARK OFFICE
CERTIFICATE OF CORRECTION

PATENT NO. : 6,323,206 B1
DATED : November 27, 2001
INVENTOR(S) : Charles F. Schwender, Charles R. Mackay, Julia C. Pinto and Walter Newman It is certified that error appears in the above-identified patent and that said Letters Patent is hereby corrected as shown below:

<u>Column 23,</u>
Line 18, delete "(aromatic soup)" and insert -- (aromatic group) --.

Signed and Sealed this

Second Day of April, 2002

Attest:

JAMES E. ROGAN
Attesting Officer
Director of the United States Patent and Trademark Office